United States Patent
Tomono et al.

(10) Patent No.: US 7,622,291 B2
(45) Date of Patent: Nov. 24, 2009

(54) AGARASE AND GENE THEREOF

(75) Inventors: Jun Tomono, Shiga (JP); Hiroaki Sagawa, Shiga (JP); Ikunoshin Kato, Kyoto (JP)

(73) Assignee: Takara Bio Inc., Shiga (JP)

( * ) Notice: Subject to any disclaimer, the term of this patent is extended or adjusted under 35 U.S.C. 154(b) by 0 days.

(21) Appl. No.: 11/948,650

(22) Filed: Nov. 30, 2007

(65) Prior Publication Data

US 2008/0096249 A1 Apr. 24, 2008

Related U.S. Application Data

(62) Division of application No. 10/467,824, filed as application No. PCT/JP02/01700 on Feb. 26, 2002, now Pat. No. 7,329,524.

(30) Foreign Application Priority Data

Feb. 27, 2001 (JP) ............... 2001-052315
Oct. 24, 2001 (JP) ............... 2001-325796

(51) Int. Cl.
C07H 21/04 (2006.01)
C12N 1/21 (2006.01)
C12N 15/63 (2006.01)
C12P 19/26 (2006.01)
C12N 9/24 (2006.01)
C12N 9/40 (2006.01)

(52) U.S. Cl. ............... 435/200; 435/208; 435/252.3; 435/320.1; 435/84; 536/23.2

(58) Field of Classification Search ............... 435/200, 435/208, 252.3, 320.1; 536/23.2
See application file for complete search history.

(56) References Cited

U.S. PATENT DOCUMENTS 5,869,310 A 2/1999 Knuth et al.
6,001,636 A 12/1999 Knuth et al.

FOREIGN PATENT DOCUMENTS

| EP | 0743363 | 11/1996 |
| EP | 1156104 | 11/2001 |
| EP | 1156104 A1 | 11/2001 |
| FR | 2786500 A | 6/2009 |
| GB | 2354000 | 3/2001 |
| JP | 7322878 | 12/1995 |

OTHER PUBLICATIONS

Kwan, S., at al., *Enzymic Cleavage of the α-Linkages in Agarose, to Yield Agaro-Oligosaccharides.* Carbohydrate Research, vol. 66 (1978), pp. 207-212.
Potin. P., et al., *Purification and Characterization of the α-agarase from Alteromonas agarlyticus (Cataldi) comb. nov., strain GJ1B.* European Journal of Biochemistry, No. 214 (1993), pp. 599-607.
Database EMBL 'Online!, Jan. 21, 2000, retrieved from EMBL, Database accession No. AF121273 XP002271973 Sequence of alpha-agarase from *Alteromonas agarilytica.*
Database EMBL Online, Database Accession No. M73783 XP 002271971, Sequence of Beta-Agarase I Gene from Pseudomonas Atlantica, Mar. 12, 1996.
Database EMBL Online, Database Accession No. U61972 XP 002271972, Sequence of Beta-Agarase Gene from Aeromonas sp., Oct. 20, 1999.
Vera, et al., "Identification of a Marine Agarolytic Pseudoalteromonas Isolate and Characterization of Its Extracellular Agarase", Applied and Environmental Microbiology. Nov. 1998, vol. 64, No. 11, 4378-4383.
Hassairi at al., *Bioresource Tech.*, 79 :47-51 (2001).

*Primary Examiner*—Tekchand Saidha
(74) *Attorney, Agent, or Firm*—Browdy and Neimark, PLLC

(57) ABSTRACT

Production of efficiently producing agaro-oligosaccharide; a polypeptide having an agarase activity which is usable in, for example, efficiently extracting a substance such as a nucleic acid from an agarose gel; the amino acid sequence of the polypeptide; a gene encoding the polypeptide; a process for producing the polypeptide; a process for producing agaro-oligosaccharide; and a process for extracting a substance such as a nucleic acid from an agarose gel.

17 Claims, No Drawings

SEQUENCE LISTING

```
<160> NUMBER OF SEQ ID NOS: 34

<210> SEQ ID NO 1
<211> LENGTH: 13
<212> TYPE: PRT
<213> ORGANISM: Unknown
<220> FEATURE:
<223> OTHER INFORMATION: Unknown
<220> FEATURE:
<221> NAME/KEY: misc_feature
<223> OTHER INFORMATION: N-terminal amino acid sequence of agarase I
<220> FEATURE:
<221> NAME/KEY: misc_feature
<222> LOCATION: (3)..(3)
<223> OTHER INFORMATION: Xaa can be any naturally occurring amino acid

<400> SEQUENCE: 1

Ala Asp Xaa Asp Gly Val Pro Ile Pro Ala Pro Ala Gly
1               5                   10

<210> SEQ ID NO 2
<211> LENGTH: 10
<212> TYPE: PRT
<213> ORGANISM: Unknown
<220> FEATURE:
<223> OTHER INFORMATION: Unknown
<220> FEATURE:
<221> NAME/KEY: misc_feature
<223> OTHER INFORMATION: N-terminal amino acid sequence of agarase II

<400> SEQUENCE: 2

Glu Thr Ile Val Leu Gln Ala Glu Ser Phe
1               5                   10

<210> SEQ ID NO 3
<211> LENGTH: 8
<212> TYPE: PRT
<213> ORGANISM: Unknown
<220> FEATURE:
<223> OTHER INFORMATION: Unknown
<220> FEATURE:
<221> NAME/KEY: misc_feature
<223> OTHER INFORMATION: partial amino acid sequence of agarase I

<400> SEQUENCE: 3

Pro Thr Pro Ala Glu Leu Ala Asp
1               5

<210> SEQ ID NO 4
<211> LENGTH: 10
```

```
<212> TYPE: PRT
<213> ORGANISM: Unknown
<220> FEATURE:
<223> OTHER INFORMATION: Unknown
<220> FEATURE:
<221> NAME/KEY: misc_feature
<223> OTHER INFORMATION: partial amino acid sequence of agarase I

<400> SEQUENCE: 4

Ala Thr Ser Asn Gly Ala Asn Ile Val Gln
1               5                   10

<210> SEQ ID NO 5
<211> LENGTH: 10
<212> TYPE: PRT
<213> ORGANISM: Unknown
<220> FEATURE:
<223> OTHER INFORMATION: Unknown
<220> FEATURE:
<221> NAME/KEY: misc_feature
<223> OTHER INFORMATION: partial amino acid sequence of agarase II

<400> SEQUENCE: 5

Pro Ser His Ser Val Thr Leu Pro Ala Gly
1               5                   10

<210> SEQ ID NO 6
<211> LENGTH: 10
<212> TYPE: PRT
<213> ORGANISM: Unknown
<220> FEATURE:
<223> OTHER INFORMATION: Unknown
<220> FEATURE:
<221> NAME/KEY: misc_feature
<223> OTHER INFORMATION: partial amino acid sequence of agarase II

<400> SEQUENCE: 6

Leu Met Phe Asp Thr Gln Thr Asn Ser Thr
1               5                   10

<210> SEQ ID NO 7
<211> LENGTH: 10
<212> TYPE: PRT
<213> ORGANISM: Unknown
<220> FEATURE:
<223> OTHER INFORMATION: Unknown
<220> FEATURE:
<221> NAME/KEY: misc_feature
<223> OTHER INFORMATION: partial amino acid sequence of agarase II

<400> SEQUENCE: 7

Phe Gly Glu Val Leu Asp Tyr Ile Arg Gln
1               5                   10

<210> SEQ ID NO 8
<211> LENGTH: 20
<212> TYPE: DNA
<213> ORGANISM: Artificial
<220> FEATURE:
<223> OTHER INFORMATION: Unknown
<220> FEATURE:
<221> NAME/KEY: misc_feature
<223> OTHER INFORMATION: PCR primer 1
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
```

```
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 8
gayggngtnc cnathccngc                                               20

<210> SEQ ID NO 9
<211> LENGTH: 29
<212> TYPE: DNA
<213> ORGANISM: Artificial
<220> FEATURE:
<223> OTHER INFORMATION: Unknown
<220> FEATURE:
<221> NAME/KEY: misc_feature
<223> OTHER INFORMATION: PCR primer 2
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t

<400> SEQUENCE: 9
gayggngtnc cnathccngc nccngcngg                                     29

<210> SEQ ID NO 10
<211> LENGTH: 26
<212> TYPE: DNA
<213> ORGANISM: Artificial
<220> FEATURE:
<223> OTHER INFORMATION: Unknown
<220> FEATURE:
<221> NAME/KEY: misc_feature
<223> OTHER INFORMATION: PCR primer 3

<400> SEQUENCE: 10
gcattgatat aactatcgtt ccaacg                                        26

<210> SEQ ID NO 11
<211> LENGTH: 24
<212> TYPE: DNA
<213> ORGANISM: Artificial
<220> FEATURE:
<223> OTHER INFORMATION: Unknown
<220> FEATURE:
```

```
<221> NAME/KEY: misc_feature
<223> OTHER INFORMATION: PCR primer 4

<400> SEQUENCE: 11
cgtctgatat ggattgcaat tgcc                                              24

<210> SEQ ID NO 12
<211> LENGTH: 26
<212> TYPE: DNA
<213> ORGANISM: Artificial
<220> FEATURE:
<223> OTHER INFORMATION: Unknown
<220> FEATURE:
<221> NAME/KEY: misc_feature
<223> OTHER INFORMATION: PCR primer 5

<400> SEQUENCE: 12
gccgctgcac attattattg atatgg                                            26

<210> SEQ ID NO 13
<211> LENGTH: 25
<212> TYPE: DNA
<213> ORGANISM: Artificial
<220> FEATURE:
<223> OTHER INFORMATION: Unknown
<220> FEATURE:
<221> NAME/KEY: misc_feature
<223> OTHER INFORMATION: PCR primer 6

<400> SEQUENCE: 13
caacaccagc tgagcttgca gaccc                                             25

<210> SEQ ID NO 14
<211> LENGTH: 23
<212> TYPE: DNA
<213> ORGANISM: Artificial
<220> FEATURE:
<223> OTHER INFORMATION: Unknown
<220> FEATURE:
<221> NAME/KEY: misc_feature
<223> OTHER INFORMATION: PCR primer 7
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 14
garacnathg tnytncargc nga                                               23

<210> SEQ ID NO 15
<211> LENGTH: 26
<212> TYPE: DNA
<213> ORGANISM: Artificial
<220> FEATURE:
<223> OTHER INFORMATION: Unknown
<220> FEATURE:
<221> NAME/KEY: misc_feature
<223> OTHER INFORMATION: PCR primer 8
<220> FEATURE:
```

```
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 15
gtnswrttng tytgngtrtc raacat                                        26

<210> SEQ ID NO 16
<211> LENGTH: 28
<212> TYPE: DNA
<213> ORGANISM: Artificial
<220> FEATURE:
<223> OTHER INFORMATION: Unknown
<220> FEATURE:
<221> NAME/KEY: misc_feature
<223> OTHER INFORMATION: PCR primer 9

<400> SEQUENCE: 16
ctcaatgtca tattcccccc cttcagcg                                      28

<210> SEQ ID NO 17
<211> LENGTH: 29
<212> TYPE: DNA
<213> ORGANISM: Artificial
<220> FEATURE:
<223> OTHER INFORMATION: Unknown
<220> FEATURE:
<221> NAME/KEY: misc_feature
<223> OTHER INFORMATION: PCR primer 10

<400> SEQUENCE: 17
cgcgttttgt ccatttacgc tgtatatcg                                     29

<210> SEQ ID NO 18
<211> LENGTH: 27
<212> TYPE: DNA
<213> ORGANISM: Artificial
<220> FEATURE:
<223> OTHER INFORMATION: Unknown
<220> FEATURE:
<221> NAME/KEY: misc_feature
<223> OTHER INFORMATION: PCR primer 11

<400> SEQUENCE: 18
acccgcagcc gcattatgtg caaacac                                       27

<210> SEQ ID NO 19
<211> LENGTH: 27
<212> TYPE: DNA
<213> ORGANISM: Artificial
<220> FEATURE:
<223> OTHER INFORMATION: Unknown
<220> FEATURE:
<221> NAME/KEY: misc_feature
<223> OTHER INFORMATION: PCR primer 12

<400> SEQUENCE: 19
gcatgacctt tatgggttac ttgtcgc                                       27

<210> SEQ ID NO 20
<211> LENGTH: 1314
```

```
<212> TYPE: DNA
<213> ORGANISM: Unknown
<220> FEATURE:
<223> OTHER INFORMATION: Unknown
<220> FEATURE:
<221> NAME/KEY: misc_feature
<223> OTHER INFORMATION: nucleotides sequence of ORF in agarase I gene

<400> SEQUENCE: 20
atgcttcaga aaatcacact atgcgcgtct ctagttttaa ctagtacaac tgttttgcc       60
gcagattggg atggcgtacc aatcccagca ccagcgggtc aaaataaaac ttggcaattg     120
caatccatat cagacgactt taactacaca gcttcagcaa ataacaaacc aagcgctttt    180
acaagccgtt ggaacgatag ttatatcaat gcatggaaag ggcctggcga tacagaattt    240
agctcaggtc actcgtacac aaattcaggt aaactggctt tgcaagcagc tgaaaaacct    300
ggcacagata aggtttatgc aggtattatt tcttcaaaac aaacattcac ttatccgttg    360
tatatagaag cacgcgcaaa atcgaccaat aatacgatgg ccaatgcagt ttggatgtta    420
agtgccgatt caacgcaaga attagatgca atggaagctt acggcagtga tagaccgggc    480
caagaatggt tcgatcgccg tatgcatgta agccatcacg tatttattcg cgaaccattc    540
caagactatc aacccaaaga tgcgggttct tggatatata atgaacaagc gccttggcgc    600
gttgcctatc ataactatgg gatgcattgg aaagatcctt ggaatgttga ttactacata    660
gatggtgtgc ttgttagaag tgtttccggt caacaaatga tcgatccaca caactacacc    720
aacggtacgg gtgtaaacaa gccgctgcac attattattg atatggaaca ccaagactgg    780
cgtgatgtta aaccaacacc agctgagctt gcagaccctg cgagaagtat ttttttatgta   840
gattggatcc gagtatacaa gccaactgat tcagcagctt cagcacccac accccctaca   900
ggtgcaacat ctcttaaggc tagacatagc aacaaatgct tagatttatc tgctggtaat   960
tctgcgaatg gtgcaaacat gcaacaatgg aattgcaacg cgacgaacac aaaccaagat  1020
ataacctttg tcgccaaagg tgctggttat tacgaaatga aaaccaaaca caataaatgt  1080
ttagatgttg cgggtaaagc aaccagcaat ggcgcgaata tagtgcagtg gaattgttac  1140
aacgggacta ccagcaatt taaattacta gacaaaggca atggttggtt ccaactacaa   1200
gcaaaacata gtggcaagtg tttagaaatt gcaaattctg caaccaccaa tggtgccaac  1260
gtgcaacagt gggcgtgtgg aaatagcaac aatcagcagt ggaaattcca gtaa         1314

<210> SEQ ID NO 21
<211> LENGTH: 3270
<212> TYPE: DNA
<213> ORGANISM: Unknown
<220> FEATURE:
<223> OTHER INFORMATION: Unknown
<220> FEATURE:
<221> NAME/KEY: misc_feature
<223> OTHER INFORMATION: nucleotides sequence of ORF in agarase II gene

<400> SEQUENCE: 21
atgtttaaaa ctaaacgttc tctgctgagc tctagtattg cgctttcact ggctttactc       60
ggcactaaag cgcatgcaga gactatagtc ttgcaagctg aatcgtttga taactccggc     120
ggtacgtatg atgacggcca acccaaccct gtcacgatat acagcgtaaa tggacaaaac    180
gcgattaatt ttgttaacgc gggtgatttt gtcgatttta atattaacgc tgaagggggg    240
gaatatgaca ttgagtattt agtcggcaca agtgtccaat caggtcctag tattgaagtg    300
ctcgttaata ctaatggtgc atgggaaagc caaggcacag tcgctgtacc gttaaccagt    360
```

```
tgggacgatt tccagcctct caaacccagc cattccgtaa ctttgccagc aggtgcttca      420
accattcgtt tgcacgcaat tggttcgact tggcaatgga acatggagtc ttttctttta      480
acacaagttg taccgcttga gccagaaaca cccgttgatg tagacgatat tgttattaac      540
ctagaaaact ttatctttac agacaaagaa ggagcagcta tttcaggtga taccatcgtc      600
ggttttggtg taacaaactc aggtataaat tttaatacgg tcggcgatta tgccgactac      660
acagtaaact ttactgaagc aggtacatac aacgcgacac tggctgctgg ttcacccatg      720
acaggtcaaa tcggtgcaca aattatcatg gataattcgg ttgccgcgtc atcgttactt      780
gcatctacag gtggctggga taattatgtc gactttgatc tcagtggcga cattgttata      840
ccaacgcccg gtacttacac tgtacgatta caaagttatg gtagcgcgaa ttggcagtgg      900
aacgcagata cactaacgct tagttatata tctggagaaa ccggcgacgg caatccaagt      960
ccaccacaag aaggtgattt gattgttgaa ttagaagatt tcgttaatac aggtacaacc     1020
ggccgcgttg gaggcgatag cgttgaaggc tttggcgcaa cagcaactgg cgtgaactgg     1080
gtgaccaatg gtgattatgg tgactacaac ataaccttttg cagagcctgg tacctatcgt     1140 gccttttta cctattcagc cgccagtgca ggtagttacg cgctcgtgt agatgtaaat     1200 ggtgaacccg tagcatgggg ctattttgct gaaacaggca gttgggatgt tgcgtctgaa     1260
gttgagcttt atggtggata ctttgttatt gaccaagcag gccaagcgaa tttgcgcgta     1320
gaagcaattg gtggatcaga ttggcagtgg ggcggtgata aactgcggat aaacccgtgta     1380 ggtgatgttt catatgtccc tgaacgtcac tataatccga acgatcacta cgtggaagaa     1440
gttgaaggac cacaaacaca aattacctat ctaaaaccac caattgacat tcctaccaat     1500
aaaaaagttc taaatcaga cgtttggtat acgtatccac aaaaccggga actggaaggt     1560
tttgatgatt ttggcgcaac tggcgcattc tggggacatc cgccagagca tgatttttat     1620
gaagaaaccg ttattatgga ttgggcagtc aatgtcgttg atacgttcca aagtgaaggt     1680
tttgagtata ctgctcgcgg cgaatttgac tggggttatg gttggttcac cgagtacgtg     1740
acaaacccgc agccgcatta tgtgcaaaca cttgacgatc gcaatgtgcg catgaccttt     1800
atgggttact tgtcgcacaa cggttataat aacaactggt taagtaatca tagtccagca     1860
tttgtacctt tcatgaaatc acaggttgat caaatattga aagcgtatcc ggacaagctg     1920
atgtttgata cacaaaccaa ctcaacccgt tcaaccgaca tgcgtacctt tggtggtgac     1980
ttctcgccat atgccatgga aaacttccgc atttggttag ataaaaaata cagtagtaac     2040
gagttggcca atatgggtat taataatatt caaacgtttg attacaaaca gcacttgtta     2100
aatgccggtg tgacacatca atcattcatg aatgcggcag atacattatc tggaaacgta     2160
ccattacttg aagatttcat ttattttaat cgtgatgtat ggaaccaaaa atttggtgaa     2220
gtattagatt atattcgcca gcaacgtcca gacatagaaa ttggtgcgag cacacatttg     2280
tttgaatctc gtggttatat atttaacgag aatatcacct tcttatcagg tgagctcaac     2340
ttaggtgcga gaaccactat ctctgaacta ccaacgaata tccttgtaca cttaaaaggg     2400
gcgcaggcag tagataaaac gttagcatac ttcccgtatc cttgggagtt tgacgaactt     2460
cgtttgcaag acgcaccgcg ttttggccgt ggttgggtcg cgcaagctta tgcttacggt     2520
ggtttattct cgattccggc taatgtttgg gttggtggtg aagtttggac ttggtctccg     2580
ggcgctgata actatcgtga tatttaccag tttgtacgag cgcaagcaga cttgttagac     2640
ggttatacct catattcaaa agtaggtctt gtgcacgcga tgttctcatc gatgaaagcg     2700
ggctttattg atgggggtaa ccaaattcaa tcaagcgtta aattactgac tgaagataat     2760
```

```
attaactttg atttattggt gtttggtgat gcgggttatc ctgttgtccc acgagctgaa    2820
gactttgata aattcgaaca tatcttcttc gatggtgatc aacaatactt aaccgctgaa    2880
caacaagcta tattagatgc acaaggtagc aaagtaagac acattggcca gcgcggtact    2940
ttaagcggta tcgaaataga tgtcagtatc aatggtagtg tttctaacga aacagtatct    3000
gcggtatctc gcattcatga aaccaatgca aatgcgccat atgttgtgca cttggttaat    3060
cgtccatttg caggcggtgt aacgccaaca ttaaatggcg tagaagtggc aattccgcaa    3120
ggttatttcc cggatacagt aacatcggcg acattacact taccggatgg taccagtacc    3180
aacttaagtg tttcgacaaa cgccgaaggt gatgctgtcg ttacggtaaa taacttagaa    3240
gtttggggta ttttagaatt agcgcactaa                                     3270
```

<210> SEQ ID NO 22
<211> LENGTH: 437
<212> TYPE: PRT
<213> ORGANISM: Unknown
<220> FEATURE:
<223> OTHER INFORMATION: Unknown
<220> FEATURE:
<221> NAME/KEY: misc_feature
<223> OTHER INFORMATION: amino acids sequence of agarase I

<400> SEQUENCE: 22

```
Met Leu Gln Lys Ile Thr Leu Cys Ala Ser Leu Val Leu Thr Ser Thr
1               5                   10                  15

Thr Val Phe Ala Ala Asp Trp Asp Gly Val Pro Ile Pro Ala Pro Ala
            20                  25                  30

Gly Gln Asn Lys Thr Trp Gln Leu Gln Ser Ile Ser Asp Asp Phe Asn
        35                  40                  45

Tyr Thr Ala Ser Ala Asn Asn Lys Pro Ser Ala Phe Thr Ser Arg Trp
    50                  55                  60

Asn Asp Ser Tyr Ile Asn Ala Trp Lys Gly Pro Gly Asp Thr Glu Phe
65                  70                  75                  80

Ser Ser Gly His Ser Tyr Thr Asn Ser Gly Lys Leu Ala Leu Gln Ala
                85                  90                  95

Ala Glu Lys Pro Gly Thr Asp Lys Val Tyr Ala Gly Ile Ile Ser Ser
            100                 105                 110

Lys Gln Thr Phe Thr Tyr Pro Leu Tyr Ile Glu Ala Arg Ala Lys Ser
        115                 120                 125

Thr Asn Asn Thr Met Ala Asn Ala Val Trp Met Leu Ser Ala Asp Ser
    130                 135                 140

Thr Gln Glu Leu Asp Ala Met Glu Ala Tyr Gly Ser Asp Arg Pro Gly
145                 150                 155                 160

Gln Glu Trp Phe Asp Arg Arg Met His Val Ser His Val Phe Ile
                165                 170                 175

Arg Glu Pro Phe Gln Asp Tyr Gln Pro Lys Asp Ala Gly Ser Trp Ile
            180                 185                 190

Tyr Asn Glu Gln Ala Pro Trp Arg Val Ala Tyr His Asn Tyr Gly Met
        195                 200                 205

His Trp Lys Asp Pro Trp Asn Val Asp Tyr Tyr Ile Asp Gly Val Leu
    210                 215                 220

Val Arg Ser Val Ser Gly Gln Gln Met Ile Asp Pro His Asn Tyr Thr
225                 230                 235                 240

Asn Gly Thr Gly Val Asn Lys Pro Leu His Ile Ile Ile Asp Met Glu
                245                 250                 255
```

```
His Gln Asp Trp Arg Asp Val Lys Pro Thr Pro Ala Glu Leu Ala Asp
            260                 265                 270

Pro Ala Arg Ser Ile Phe Tyr Val Asp Trp Ile Arg Val Tyr Lys Pro
        275                 280                 285

Thr Asp Ser Ala Ala Ser Ala Pro Thr Pro Pro Thr Gly Ala Thr Ser
    290                 295                 300

Leu Lys Ala Arg His Ser Asn Lys Cys Leu Asp Leu Ser Ala Gly Asn
305                 310                 315                 320

Ser Ala Asn Gly Ala Asn Met Gln Gln Trp Asn Cys Asn Ala Thr Asn
            325                 330                 335

Thr Asn Gln Asp Ile Thr Phe Val Ala Lys Gly Ala Gly Tyr Tyr Glu
            340                 345                 350

Met Lys Thr Lys His Asn Lys Cys Leu Asp Val Ala Gly Lys Ala Thr
            355                 360                 365

Ser Asn Gly Ala Asn Ile Val Gln Trp Asn Cys Tyr Asn Gly Thr Asn
370                 375                 380

Gln Gln Phe Lys Leu Leu Asp Lys Gly Asn Gly Trp Phe Gln Leu Gln
385                 390                 395                 400

Ala Lys His Ser Gly Lys Cys Leu Glu Ile Ala Asn Ser Ala Thr Thr
            405                 410                 415

Asn Gly Ala Asn Val Gln Gln Trp Ala Cys Gly Asn Ser Asn Asn Gln
            420                 425                 430

Gln Trp Lys Phe Gln
            435

<210> SEQ ID NO 23
<211> LENGTH: 1089
<212> TYPE: PRT
<213> ORGANISM: Unknown
<220> FEATURE:
<223> OTHER INFORMATION: Unknown
<220> FEATURE:
<221> NAME/KEY: misc_feature
<223> OTHER INFORMATION: amino acids sequence of agarase II

<400> SEQUENCE: 23

Met Phe Lys Thr Lys Arg Ser Leu Leu Ser Ser Ile Ala Leu Ser
1               5                   10                  15

Leu Ala Leu Leu Gly Thr Lys Ala His Ala Glu Thr Ile Val Leu Gln
            20                  25                  30

Ala Glu Ser Phe Asp Asn Ser Gly Gly Thr Tyr Asp Asp Gly Gln Pro
        35                  40                  45

Asn Pro Val Thr Ile Tyr Ser Val Asn Gly Gln Asn Ala Ile Asn Phe
    50                  55                  60

Val Asn Ala Gly Asp Phe Val Asp Phe Asn Ile Asn Ala Glu Gly Gly
65                  70                  75                  80

Glu Tyr Asp Ile Glu Tyr Leu Val Gly Thr Ser Val Gln Ser Gly Pro
                85                  90                  95

Ser Ile Glu Val Leu Val Asn Thr Asn Gly Ala Trp Glu Ser Gln Gly
            100                 105                 110

Thr Val Ala Val Pro Leu Thr Ser Trp Asp Asp Phe Gln Pro Leu Lys
        115                 120                 125

Pro Ser His Ser Val Thr Leu Pro Ala Gly Ala Ser Thr Ile Arg Leu
    130                 135                 140

His Ala Ile Gly Ser Thr Trp Gln Trp Asn Met Glu Ser Phe Ser Leu
145                 150                 155                 160
```

-continued

```
Thr Gln Val Val Pro Leu Glu Pro Thr Pro Val Asp Val Asp Asp
            165                 170                 175
Ile Val Ile Asn Leu Glu Asn Phe Ile Phe Thr Asp Lys Glu Gly Ala
        180                 185                 190
Ala Ile Ser Gly Asp Thr Ile Val Gly Phe Gly Val Thr Asn Ser Gly
    195                 200                 205
Ile Asn Phe Asn Thr Val Gly Asp Tyr Ala Asp Tyr Thr Val Asn Phe
    210                 215                 220
Thr Glu Ala Gly Thr Tyr Asn Ala Thr Leu Ala Ala Gly Ser Pro Met
225                 230                 235                 240
Thr Gly Gln Ile Gly Ala Gln Ile Ile Met Asp Asn Ser Val Ala Ala
                245                 250                 255
Ser Ser Leu Leu Ala Ser Thr Gly Gly Trp Asp Asn Tyr Val Asp Phe
                260                 265                 270
Asp Leu Ser Gly Asp Ile Val Ile Pro Thr Pro Gly Thr Tyr Thr Val
            275                 280                 285
Arg Leu Gln Ser Tyr Gly Ser Ala Asn Trp Gln Trp Asn Ala Asp Thr
        290                 295                 300
Leu Thr Leu Ser Tyr Ile Ser Gly Glu Thr Gly Asp Gly Asn Pro Ser
305                 310                 315                 320
Pro Pro Gln Glu Gly Asp Leu Ile Val Glu Leu Glu Asp Phe Val Asn
                325                 330                 335
Thr Gly Thr Thr Gly Arg Val Gly Gly Asp Ser Val Glu Gly Phe Gly
                340                 345                 350
Ala Thr Ala Thr Gly Val Asn Trp Val Thr Asn Gly Asp Tyr Gly Asp
            355                 360                 365
Tyr Asn Ile Thr Phe Ala Glu Pro Gly Thr Tyr Arg Ala Phe Phe Thr
        370                 375                 380
Tyr Ser Ala Ala Ser Ala Gly Ser Tyr Gly Ala Arg Val Asp Val Asn
385                 390                 395                 400
Gly Glu Pro Val Ala Trp Gly Tyr Phe Ala Glu Thr Gly Ser Trp Asp
                405                 410                 415
Val Ala Ser Glu Val Glu Leu Tyr Gly Gly Tyr Phe Val Ile Asp Gln
                420                 425                 430
Ala Gly Gln Ala Asn Leu Arg Val Glu Ala Ile Gly Gly Ser Asp Trp
            435                 440                 445
Gln Trp Gly Gly Asp Lys Leu Arg Ile Thr Arg Val Gly Asp Val Ser
        450                 455                 460
Tyr Val Pro Glu Arg His Tyr Asn Pro Asn Asp His Tyr Val Glu Glu
465                 470                 475                 480
Val Glu Gly Pro Gln Thr Gln Ile Thr Tyr Leu Lys Pro Pro Ile Asp
                485                 490                 495
Ile Pro Thr Asn Lys Lys Val Leu Lys Ser Asp Val Trp Tyr Thr Tyr
            500                 505                 510
Pro Gln Asn Arg Glu Leu Glu Gly Phe Asp Asp Phe Gly Ala Thr Gly
        515                 520                 525
Ala Phe Trp Gly His Pro Pro Glu His Asp Phe Tyr Glu Glu Thr Val
    530                 535                 540
Ile Met Asp Trp Ala Val Asn Val Val Asp Thr Phe Gln Ser Glu Gly
545                 550                 555                 560
Phe Glu Tyr Thr Ala Arg Gly Glu Phe Asp Trp Gly Tyr Gly Trp Phe
                565                 570                 575
```

-continued

```
Thr Glu Tyr Val Thr Asn Pro Gln Pro His Tyr Val Gln Thr Leu Asp
            580                 585                 590

Asp Arg Asn Val Arg Met Thr Phe Met Gly Tyr Leu Ser His Asn Gly
            595                 600                 605

Tyr Asn Asn Asn Trp Leu Ser Asn His Ser Pro Ala Phe Val Pro Phe
            610                 615                 620

Met Lys Ser Gln Val Asp Gln Ile Leu Lys Ala Tyr Pro Asp Lys Leu
625                 630                 635                 640

Met Phe Asp Thr Gln Thr Asn Ser Thr Arg Ser Thr Asp Met Arg Thr
                645                 650                 655

Phe Gly Gly Asp Phe Ser Pro Tyr Ala Met Glu Asn Phe Arg Ile Trp
                660                 665                 670

Leu Asp Lys Lys Tyr Ser Ser Asn Glu Leu Ala Asn Met Gly Ile Asn
                675                 680                 685

Asn Ile Gln Thr Phe Asp Tyr Lys Gln His Leu Leu Asn Ala Gly Val
            690                 695                 700

Thr His Gln Ser Phe Met Asn Ala Ala Asp Thr Leu Ser Gly Asn Val
705                 710                 715                 720

Pro Leu Leu Glu Asp Phe Ile Tyr Phe Asn Arg Asp Val Trp Asn Gln
                725                 730                 735

Lys Phe Gly Glu Val Leu Asp Tyr Ile Arg Gln Gln Arg Pro Asp Ile
                740                 745                 750

Glu Ile Gly Ala Ser Thr His Leu Phe Glu Ser Arg Gly Tyr Ile Phe
                755                 760                 765

Asn Glu Asn Ile Thr Phe Leu Ser Gly Glu Leu Asn Leu Gly Ala Arg
            770                 775                 780

Thr Thr Ile Ser Glu Leu Pro Thr Asn Ile Leu Val His Leu Lys Gly
785                 790                 795                 800

Ala Gln Ala Val Asp Lys Thr Leu Ala Tyr Phe Pro Tyr Pro Trp Glu
                805                 810                 815

Phe Asp Glu Leu Arg Leu Gln Asp Ala Pro Arg Phe Gly Arg Gly Trp
                820                 825                 830

Val Ala Gln Ala Tyr Ala Tyr Gly Gly Leu Phe Ser Ile Pro Ala Asn
                835                 840                 845

Val Trp Val Gly Gly Glu Val Trp Thr Trp Ser Pro Gly Ala Asp Asn
            850                 855                 860

Tyr Arg Asp Ile Tyr Gln Phe Val Arg Ala Gln Ala Asp Leu Leu Asp
865                 870                 875                 880

Gly Tyr Thr Ser Tyr Ser Lys Val Gly Leu Val His Ala Met Phe Ser
                885                 890                 895

Ser Met Lys Ala Gly Phe Ile Asp Gly Gly Asn Gln Ile Gln Ser Ser
                900                 905                 910

Val Lys Leu Leu Thr Glu Asp Asn Ile Asn Phe Asp Leu Leu Val Phe
            915                 920                 925

Gly Asp Ala Gly Tyr Pro Val Val Pro Arg Ala Glu Asp Phe Asp Lys
            930                 935                 940

Phe Glu His Ile Phe Phe Asp Gly Asp Gln Tyr Leu Thr Ala Glu
945                 950                 955                 960

Gln Gln Ala Ile Leu Asp Ala Gln Gly Ser Lys Val Arg His Ile Gly
                965                 970                 975

Gln Arg Gly Thr Leu Ser Gly Ile Glu Ile Asp Val Ser Ile Asn Gly
                980                 985                 990

Ser Val Ser Asn Glu Thr Val Ser  Ala Val Ser Arg Ile  His Glu Thr
```

-continued

```
                995              1000             1005

Asn Ala  Asn Ala Pro Tyr Val  Val His Leu Val Asn  Arg Pro Phe
    1010             1015             1020

Ala Gly  Gly Val Thr Pro Thr  Leu Asn Gly Val Glu  Val Ala Ile
    1025             1030             1035

Pro Gln  Gly Tyr Phe Pro Asp  Thr Val Thr Ser Ala  Thr Leu His
    1040             1045             1050

Leu Pro  Asp Gly Thr Ser Thr  Asn Leu Ser Val Ser  Thr Asn Ala
    1055             1060             1065

Glu Gly  Asp Ala Val Val Thr  Val Asn Asn Leu Glu  Val Trp Gly
    1070             1075             1080

Ile Leu  Glu Leu Ala His
    1085

<210> SEQ ID NO 24
<211> LENGTH: 38
<212> TYPE: DNA
<213> ORGANISM: Artificial
<220> FEATURE:
<223> OTHER INFORMATION: Unknown
<220> FEATURE:
<221> NAME/KEY: misc_feature
<223> OTHER INFORMATION: PCR primer 13

<400> SEQUENCE: 24
ctgtttttgc cgaattcggc agattgggat ggcgtacc                          38

<210> SEQ ID NO 25
<211> LENGTH: 38
<212> TYPE: DNA
<213> ORGANISM: Artificial
<220> FEATURE:
<223> OTHER INFORMATION: Unknown
<220> FEATURE:
<221> NAME/KEY: misc_feature
<223> OTHER INFORMATION: PCR primer 14

<400> SEQUENCE: 25
gctgaaccct ctgcagtatt caacaacaac tgttgagc                          38

<210> SEQ ID NO 26
<211> LENGTH: 39
<212> TYPE: DNA
<213> ORGANISM: Artificial
<220> FEATURE:
<223> OTHER INFORMATION: Unknown
<220> FEATURE:
<221> NAME/KEY: misc_feature
<223> OTHER INFORMATION: PCR primer 15

<400> SEQUENCE: 26
caactgtttt tgccatatgg cagattggga tggcgtacc                         39

<210> SEQ ID NO 27
<211> LENGTH: 36
<212> TYPE: DNA
<213> ORGANISM: Artificial
<220> FEATURE:
<223> OTHER INFORMATION: Unknown
<220> FEATURE:
<221> NAME/KEY: misc_feature
<223> OTHER INFORMATION: PCR primer 16

<400> SEQUENCE: 27
gctgaaccct cctcgagtat tcaacaacaa ctgttg                            36
```

<210> SEQ ID NO 28
<211> LENGTH: 38
<212> TYPE: DNA
<213> ORGANISM: Artificial
<220> FEATURE:
<223> OTHER INFORMATION: Unknown
<220> FEATURE:
<221> NAME/KEY: misc_feature
<223> OTHER INFORMATION: PCR primer 17

<400> SEQUENCE: 28
gcgcatgcag aattcggaga ctatagtctt gcaagctg                    38

<210> SEQ ID NO 29
<211> LENGTH: 39
<212> TYPE: DNA
<213> ORGANISM: Artificial
<220> FEATURE:
<223> OTHER INFORMATION: Unknown
<220> FEATURE:
<221> NAME/KEY: misc_feature
<223> OTHER INFORMATION: PCR primer 18

<400> SEQUENCE: 29
ccaaagtatt ggatcctagg ttgttgataa acaacattg                   39

<210> SEQ ID NO 30
<211> LENGTH: 40
<212> TYPE: DNA
<213> ORGANISM: Artificial
<220> FEATURE:
<223> OTHER INFORMATION: Unknown
<220> FEATURE:
<221> NAME/KEY: misc_feature
<223> OTHER INFORMATION: PCR primer 19

<400> SEQUENCE: 30
ttgttattaa cgaattcgct agaaaacttt atctttacag                  40

<210> SEQ ID NO 31
<211> LENGTH: 40
<212> TYPE: DNA
<213> ORGANISM: Artificial
<220> FEATURE:
<223> OTHER INFORMATION: Unknown
<220> FEATURE:
<221> NAME/KEY: misc_feature
<223> OTHER INFORMATION: PCR primer 20

<400> SEQUENCE: 31
ccggcgacgg cgaattcgaa tccaagtcca ccacaagaag                  40

<210> SEQ ID NO 32
<211> LENGTH: 20
<212> TYPE: DNA
<213> ORGANISM: Artificial
<220> FEATURE:
<223> OTHER INFORMATION: Unknown
<220> FEATURE:
<221> NAME/KEY: misc_feature
<223> OTHER INFORMATION: PCR primer for 16S rRNA analysis

<400> SEQUENCE: 32
agagtttgat cctggctcag                                        20

<210> SEQ ID NO 33
<211> LENGTH: 19

```
<212> TYPE: DNA
<213> ORGANISM: Artificial
<220> FEATURE:
<223> OTHER INFORMATION: Unknown
<220> FEATURE:
<221> NAME/KEY: misc_feature
<223> OTHER INFORMATION: PCR primer for 16S rRNA analysis

<400> SEQUENCE: 33
ggctaccttg ttacgactt                                           19

<210> SEQ ID NO 34
<211> LENGTH: 40
<212> TYPE: DNA
<213> ORGANISM: Artificial
<220> FEATURE:
<223> OTHER INFORMATION: Unknown
<220> FEATURE:
<221> NAME/KEY: misc_feature
<223> OTHER INFORMATION: PCR primer 21

<400> SEQUENCE: 34
acactgtacg agaattcgtt acaaagttat ggtagcgcga                    40
```

AGARASE AND GENE THEREOF

CROSS-REFERENCE TO RELATED APPLICATIONS

The present application is a divisional of application Ser. No. 10/467,824, filed Aug. 13, 2003, and now issued as U.S. Pat. No. 7,329,524, which is the national stage under 35 U.S.C. 371 of PCT/JP02/01700, filed Feb. 26, 2002, which claims priority from JP 2001-052315, filed Feb. 27, 2001 and JP 2001-325796, filed Oct. 24, 2001. The entire contents of prior application Ser. No. 10/467,824 and PCT/JP02/01700 are herein incorporated by reference.

TECHNICAL FIELD

The present invention relates to a novel agarase which has an agarase activity at a high temperature as well as a method of production and use of the same. The present invention also relates to a polypeptide that has an agarase activity at a high temperature and a gene encoding said polypeptide. Furthermore, the present invention relates to a method for producing a polypeptide that has an agarase activity at a high temperature by genetic engineering using said gene.

Specifically, the present invention relates to an α-agarase having an activity at a high temperature which is useful for producing agarooligosaccharides with low degrees of polymerization having various physiological activities from agarose, as well as a method for producing the same and use of said enzyme. The present invention also relates to a β-agarase having an activity at a high temperature which is useful for extraction of a nucleic acid or the like from an agarose gel after agarose gel electrophoresis, as well as a method for producing the same, use of said enzyme and a method for extracting a nucleic acid or the like from an agarose gel using said enzyme.

BACKGROUND ART

Agarose is the principal constituent of agar. Agarose is a polysaccharide that has a structure in which D-galactose and 3,6-anhydro-L-galactose are alternately linked together through α-1,3 bonds and β-1,4 bonds. One must degrade agarose into smaller molecules in order to produce oligosaccharides from agar. For this purpose, methods in which agarose is chemically degraded and methods in which agarose is enzymatically digested are conventionally known. In a chemical degradation method, agarose can be hydrolyzed using an acid. In this case, α-1,3 bonds are mainly cleaved. Two types of enzymes, β-agarases which cleave β-1,4 bonds in agarose and α-agarases which cleave α-1,3 bonds in agarose, are known to digest agarose.

Oligosaccharides obtained by cleaving agarose at β-1,4 bonds are called neoagarooligosaccharides. Neoagarooligosaccharides have D-galactose at their reducing ends and their degrees of polymerization are expressed by even numbers. On the other hand, oligosaccharides obtained by cleaving agarose at α-1,3 bonds are called agarooligosaccharides. Agarooligosaccharides have 3,6-anhydro-L-galactose at their reducing ends and their degrees of polymerization are expressed by even numbers. Recently, it was shown that agarooligosaccharides which have 3,6-anhydro-L-galactose at their reducing ends have physiological activities such as an apoptosis-inducing activity, a carcinostatic activity, various antioxidant activities, an immunoregulatory activity, an anti-allergic activity, an anti-inflammatory activity and an activity of inhibiting α-glycosidase (WO 99/24447, Japanese Patent Application No. 11-11646). Based on the physiological activities, pharmaceutical compositions and functional foods or drinks containing the agarooligosaccharides as their active ingredients can be provided.

It is difficult to control the sizes of produced oligosaccharides in a method in which agarose is chemically degraded. In particular, it is quite difficult to selectively produce smaller oligosaccharides with low degrees of polymerization (e.g., T. Tokunaga et al., Bioscience & Industry, 49:734 (1991)). If a β-agarase is used, only neoagarooligosaccharides which do not have the above-mentioned physiological activities can be obtained because this enzyme cleaves only β-1,4 bonds.

It is expected that agarooligosaccharides having physiological activities are produced by using an α-agarase which has an activity of cleaving α-1,3 bonds. Known α-agarases include enzymes produced by a marine Gram-negative bacterial strain GJ1B (Carbohydrate Research, 66:207-212 (1978); this strain is indicated as *Alteromonas agarlyticus* GJ1B in European Journal of Biochemistry, 214:599-607 (1993)) and a bacterium of genus *Vibrio* (JP-A 7-322878; strain JT0107-L4). However, it is impossible to produce agarobiose which has notable physiological activities by using the α-agarase derived from *Alteromonas agarlyticus* GJ1B because the enzyme cannot digest hexasaccharides or shorter oligosaccharides. Furthermore, the α-agarase derived from the bacterium of genus *Vibrio* cannot be used for the production of agarooligosaccharides using agarose as a raw material because this enzyme exhibits its activity only on hexasaccharides and shorter oligosaccharides and does not act on agarose at all.

The present inventors studied intensively in order to obtain an enzyme that cleaves α-1,3 bonds in agarose and generates agarooligosaccharides having notable physiological activities and found two microorganisms that produce enzymes having properties suitable for this purpose. The enzymes produced by these microorganisms were isolated and their physical and chemical as well as enzymatic properties were shown. Furthermore, the present inventors isolated genes for the two enzymes, and found a method for conveniently producing polypeptides having α-agarase activities by means of genetic engineering using the genes (WO 00/50578). If one intends to obtain agarooligosaccharides by treating dissolved agarose with one of the two α-agarases, the reaction temperature needs to be lowered to about 40° C. because the optimal reaction temperatures of the enzymes are about 40° C. In this case, if the agarose concentration is high, agarose may be solidified and the enzymatic reaction may be prevented. Therefore, if such an enzyme is to be used, the treatment needs to be carried out using agarose at a low concentration. Accordingly, agarose at a high concentration cannot be treated and the productivities of agarooligosaccharides are low. Thus, a thermostable α-agarase that has an activity at a high temperature at which agarose is not solidified even if agarose is dissolved at a high concentration has been desired.

On the other hand, extraction of a nucleic acid or the like which has been subjected to treatment with a restriction enzyme or an amplification reaction from an agarose gel after agarose gel electrophoresis is widely carried out in a field of genetic engineering. A β-agarase having an optimal temperature of about 37° C. has been conventionally used for the procedure. Also in this case, the reaction temperature needs to be lowered depending on the optimal temperature of the enzyme, and the agarose concentration has to be lowered by dissolving an agarose gel containing a nucleic acid or the like to be treated in a large volume of water in order to prevent agarose from solidifying. In this case, the concentration of the nucleic acid or the like to be recovered is also lowered inevitably. The lowered concentration causes problems because it results in lowered recovery and lowered efficiency of agarose digestion as well as prolonged procedure. An agarase that can be used for a reaction at a temperature higher than the conventional one is necessary in order to solve the problems. A β-agarase derived from *Flavobacterium* sp. strain NR19 as described in U.S. Pat. No. 5,869,310 may be known as such an agarase, although its optimal temperature is not so high and the thermostability is insufficient. Thus, a thermostable β-agarase which has an activity at a high temperature at which agarose at a high concentration is not solidified has been desired.

As described above, prior art has problems regarding production of agarooligosaccharides and extraction of a material such as a nucleic acid from an agarose gel.

OBJECTS OF INVENTION

The main object of the present invention is to provide a polypeptide having an agarase activity which can be used for efficient production of agarooligosaccharides, efficient extraction of a material such as a nucleic acid from an agarose gel or the like, an amino acid sequence of said polypeptide, a gene encoding said polypeptide, a method for producing said polypeptide, a method for producing an agarooligosaccharide and a method for extracting a material such as a nucleic acid from an agarose gel.

SUMMARY OF INVENTION

In view of the problems as described above, the present inventors have studied intensively and conducted searches in order to obtain an enzyme that cleaves α-1,3 bonds in agarose at a high temperature and is useful for production of agarooligosaccharides having notable physiological activities and an enzyme that cleaves β-1,4 bonds in agarose at a high temperature and is useful for efficient extraction of a nucleic acid or the like from an agarose gel. As a result, the present inventors have successfully found a microorganism that produces two enzymes having properties suitable for the respective purposes. The enzymes were isolated from the microorganism and their physical and chemical as well as enzymatic properties were shown.

Furthermore, the present inventors have successfully isolated genes encoding the enzymes, and found methods for conveniently producing the polypeptide having an α-agarase activity and the polypeptide having a β-agarase activity of the present invention by means of genetic engineering using the genes. Thus, the present invention has been completed.

The present invention is outlined as follows. The first aspect of the present invention relates to a novel agarase which contains an amino acid sequence selected from the following, or an amino acid sequence in which one or more amino acids are substituted, deleted, added and/or inserted in said amino acid sequence:

(1) an amino acid sequence consisting of 417 residues from amino acid number 21 to amino acid number 437 in the amino acid sequence of SEQ ID NO:22; or (2) an amino acid sequence consisting of 772 residues from amino acid number 318 to amino acid number 1089 in the amino acid sequence of SEQ ID NO:23.

The agarase is exemplified by an enzyme having an activity of hydrolyzing a β-1,4 bond between D-galactose and 3,6-anhydro-L-galactose or an enzyme having an activity of hydrolyzing an α-1,3 bond between 3,6-anhydro-L-galactose and D-galactose.

The second aspect of the present invention relates to a gene encoding a polypeptide having an agarase activity. The gene encode the agarase of the first aspect. The gene is exemplified by a gene containing a nucleotide sequence consisting of 1251 nucleotides from nucleotide number 61 to nucleotide number 1311 in the nucleotide sequence of SEQ ID NO:20, or a nucleotide sequence in which one or more nucleotides are substituted, deleted, added and/or inserted in said nucleotide sequence consisting of 1251 nucleotides, or a gene containing a nucleotide sequence consisting of 2316 nucleotides from nucleotide number 952 to nucleotide number 3267 in the nucleotide sequence of SEQ ID NO:21, or a nucleotide sequence in which one or more nucleotides are substituted, deleted, added and/or inserted in said nucleotide sequence consisting of 2316 nucleotides.

The third aspect of the present invention relates to a gene which is hybridizable to the gene of the second aspect under stringent conditions and encodes the polypeptide having an agarase activity of the first aspect.

The fourth aspect of the present invention relates to a recombinant DNA molecule which contains the gene of the second or third aspect.

The fifth aspect of the present invention relates to a transformant harboring the recombinant DNA molecule of the fourth aspect.

The sixth aspect of the present invention relates to a method for producing a polypeptide having an agarase activity, the method comprising culturing a microorganism capable of producing an agarase (e.g., a microorganism belonging to the genus to which the microorganism NAB2-1-1 (FERM BP-7855) belongs); and collecting the agarase of the first aspect from the culture.

The seventh aspect of the present invention relates to a method for producing a polypeptide having an agarase activity, the method comprising culturing the transformant of the fifth aspect; and collecting the agarase of the first aspect from the culture.

The eighth aspect of the present invention relates to a method for producing an agarooligosaccharide, the method comprising digesting agarose with the agarase of the first aspect; and collecting an agarooligosaccharide from the digest.

The ninth aspect of the present invention relates to a method for extracting a material from an agarose gel, the method comprising digesting an agarose gel with the agarase of the first aspect.

The tenth aspect of the present invention relates to a kit used for the method for extracting a material from an agarose gel of the ninth aspect, which contains the agarase of the first aspect.

The eleventh aspect of the present invention relates to a method for improving thermostability of the agarase of the first aspect, the method comprising deleting a polypeptide constituting up to 30% of the agarase from the N terminus.

DETAILED DESCRIPTION OF THE INVENTION

As used herein, an oligosaccharide refers to a saccharide composed of 2 or more and 10 or less monosaccharides. An agarooligosaccharide refers to an oligosaccharide that has a structure in which D-galactose and 3,6-anhydro-L-galactose are alternately linked together through α-1,3 bonds and β-1,4 bonds and has 3,6-anhydro-L-galactose at its reducing end. A neoagarooligosaccharide refers to an oligosaccharide that has a structure in which D-galactose and 3,6-anhydro-L-galactose are alternately linked together through α-1,3 bonds and β-1,4 bonds and has 3,6-anhydro-L-galactose at its nonreducing end.

A polysaccharide refers to a saccharide other than monosaccharides and oligosaccharides.

The agarase of the present invention is one that contains an amino acid sequence consisting of 417 residues from amino acid number 21 to amino acid number 437 in the amino acid sequence of SEQ ID NO:22; or an amino acid sequence consisting of 772 residues from amino acid number 318 to amino acid number 1089 in the amino acid sequence of SEQ ID NO:23. In one embodiment, it is a polypeptide containing an amino acid sequence in which one or more amino acids are substituted, deleted, added and/or inserted in the above-mentioned amino acid sequence. For example, one having a region that has at least 70% or more, preferably 80% or more, more preferably 90% or more homology to the amino acid sequence is included. Homology can be calculated according to a known method using any computer program for such calculation such as DNASIS (Takara Shuzo).

The agarase of the present invention can act on both polysaccharides (e.g., agarose) and oligosaccharides (e.g., agarooligosaccharides and neoagarooligosaccharides). For example, the optimal reaction temperature is 45° C. or higher. There is no specific limitation concerning the enzymes of the present invention as long as they have such properties. Examples thereof include an agarase produced by a marine microorganism NAB2-1-1 (FERM BP-7855).

There is also no specific limitation concerning the cleavage mode of the agarase of the present invention. For example, the agarase may be an α-agarase which hydrolyzes an α-1,3 bond between 3,6-anhydro-L-galactose and D-galactose, or a β-agarase that hydrolyzes a β-1,4 bond between D-galactose and 3,6-anhydro-L-galactose.

The α-agarase of the present invention is an enzyme that hydrolyzes an α-1,3 bond between 3,6-anhydro-L-galactose and D-galactose and can act on both polysaccharides (e.g., agarose) and oligosaccharides (e.g., agarohexaose). There is no specific limitation concerning the enzyme of the present invention as long as it has such properties. Examples thereof include Agarase II which is an α-agarase produced by a marine microorganism NAB2-1-1 (FERM BP-7855).

Agarase II which is produced by the microorganism NAB2-1-1 is an enzyme that hydrolyzes an α-1,3 bond between 3,6-anhydro-L-galactose and D-galactose in a polysaccharide or an oligosaccharide. The enzyme acts on agarose, agarohexaose and agarooligosaccharides longer than agarohexaose (e.g., agarooctaose) as well as neoagarohexaose and neoagarooligosaccharides longer than neoagarohexaose.

The β-agarase of the present invention is an enzyme that hydrolyzes a β-1,4 bond between D-galactose and 3,6-anhydro-L-galactose and can act on both polysaccharides (e.g., agarose) and oligosaccharides (e.g., agarohexaose). There is no specific limitation concerning the enzyme of the present invention as long as it has such properties. Examples thereof include Agarase I which is a β-agarase produced by a marine microorganism NAB2-1-1 (FERM BP-7855).

Agarase I which is produced by the microorganism NAB2-1-1 is an enzyme that hydrolyzes a β-1,4 bond between D-galactose and 3,6-anhydro-L-galactose in a polysaccharide or an oligosaccharide. The enzyme acts on agarose, neoagarohexaose and neoagarooligosaccharides longer than neoagarohexaose (e.g., neoagarooctaose) as well as agarohexaose and agarooligosaccharides longer than agarohexaose.

A method for measuring the activities of the above-mentioned enzymes, and physical and chemical as well as enzymatic properties of the enzymes are described below.

(1) Enzymological Measurement Method

The activity of the agarase of the present invention is measured by conducting an enzymatic reaction using Agarose LO3 (Takara Shuzo) as a substrate and then quantifying the resulting agarotetraose or neoagarotetraose using high performance liquid chromatography. Specifically, the method for measuring an enzymatic activity used herein for measuring an activity of a purified enzyme preparation or an enzyme in the course of purification is as follows.

A solution containing agarose at a concentration of 0.2% (w/v) or 0.5% (w/v) in 20 mM Tris-HCl buffer (pH 7.2) containing 10 mM sodium chloride (in case of Agarase I) or 20 mM Tris-HCl buffer (pH 7.2) containing 10 mM calcium chloride and 10 mM sodium chloride (in case of Agarase II) is prepared. 180 μl of this solution as a substrate is mixed with 20 μl of an enzyme solution. The mixture is reacted at 50° C. for 5 to 30 minutes, preferably 10 minutes, and then heated in boiling water or at 75° C. for 1 minute to stop the reaction. 30 μl of the reaction mixture is subjected to a TSKgel α-2500 column (inner diameter: 7.8 mm; length: 300 mm; Tosoh). Agarotetraose eluted at a retention time of about 25 minutes or neoagarotetraose eluted at a retention time of about 24 minutes is quantified using 70% acetonitrile solution as an eluent at a flow rate of 0.8 ml/minute. One unit (1 U) is defined as the amount of the enzyme that produces 1 μmol of agarotetraose in 10 minutes.

(2) Optimal pH

An enzyme was allowed to act on agarose as a substrate in a reaction mixture prepared using an acetate buffer (pH 4.5), a malate buffer (pH 5.5), an acetate buffer (pH 6.0, 6.5) or a Tris-HCl buffer (pH 7.0, 7.5, 8.8). As a result, it was demonstrated that both Agarase I and Agarase II exhibit their activities of digesting agarose under weakly acidic to weakly alkaline conditions.

(3) Optimal Temperature

Agarase II of the present invention exhibits a high enzymatic activity at temperatures ranging from 45 to 55° C., and exhibits the maximal activity at about 50° C. Agarase I of the present invention exhibits a high enzymatic activity at temperatures ranging from 45 to 70° C., and exhibits the maximal activity at about 55 to 65° C.

(4) Thermostability

Remaining activities of enzyme preparations after treatment at 48° C., 50° C., 55° C., 60° C. or 65° C. for a given period were measured. As a result, Agarase II exhibited 40% of its activity after treatment at 55° C. for 10 minutes. Agarase I exhibited 100% of its activity after treatment at 60° C. for 10 minutes; 100% of its activity after treatment at 60° C. for 20 minutes; 98% of its activity after treatment at 60° C. for 30 minutes; 100% of its activity after treatment at 65° C. for 10 minutes; 95% of its activity after treatment at 65° C. for 20 minutes; 90% of its activity after treatment at 65° C. for 30 minutes; and 90% of its activity after treatment at 65° C. for 60 minutes.

(5) Ca Ion Requirement

Known agarases require calcium for exhibiting their activities. Calcium ion requirements of the respective agarases of the present invention were examined. As a result, in the absence of a calcium ion, Agarase II had 60% of the activity exhibited in the presence of a calcium ion. In the absence of a calcium ion, Agarase I had 100% of the activity exhibited in the presence of a calcium ion. Thus, both Agarase II and Agarase I exhibit their activities without the addition of a calcium ion.

Agarase II of the present invention is stabilized in the presence of $CaCl_2$, while it is not influenced by a manganese ion or a magnesium ion.

(6) Molecular Weight

The molecular weights of Agarase II and Agarase I were estimated to be about 117,000 and about 48,000, respectively, as determined by SDS-polyacrylamide gel electrophoresis (SDS-PAGE) using a 10-20% polyacrylamide gradient gel.

(7) Amino Acid Sequencing According to Edman Degradation Method

The N-terminal amino acid sequences of Agarase II and Agarase I as determined according to the Edman degradation method were Glu-Thr-Ile-Val-Leu-Gln-Ala-Glu-Ser-Phe and Ala-Asp-Xaa-Asp-Gly-Val-Pro-Ile-Pro-Ala-Pro-Ala-Gly, respectively. The N-terminal amino acid sequences of Agarase II and Agarase I are shown in SEQ ID NOS:2 and 1, respectively.

As described below, both a gene encoding Agarase II and a gene encoding Agarase I were isolated. Also, amino acid sequences encoded by these genes were determined Amino acid sequences encoded by the Agarase II gene and the Agarase I gene are shown in SEQ ID NOS:23 and 22, respectively. A polypeptide consisting of 772 amino acids from amino acid number 318 to amino acid number 1089 in the amino acid sequence of SEQ ID NO:23 exhibits the activity of the α-agarase of the present invention and a polypeptide consisting of 417 amino acids from amino acid number 21 to amino acid number 437 in the amino acid sequence of SEQ ID NO:22 exhibits the activity of the β-agarase of the present invention.

The agarase of the present invention can be purified from a culture obtained by culturing a microorganism NAB2-1-1 (FERM BP-7855). NAB2-1-1 was isolated from seawater as a bacterium that assimilates agar. It has the following microbiological properties.

[Microbiological Properties]

(1) Morphology

Artificial seawater (product name: Jamarin S; Jamarin Laboratory) was prepared. Peptone (Difco) at a concentration of 0.3% (w/v) and yeast extract (Difco) at a concentration of 0.02% (w/v) were added thereto. The pH was then adjusted to 7.8 with 3 M sodium carbonate. Agarose LO3 (Takara Shuzo) at a concentration of 0.1% (w/v) was added thereto. After sterilization in an autoclave, the above-mentioned microorganism was inoculated into the mixture, and cultured at 37° C. at 120 rpm overnight. The microorganism grown in the culture was a Gram-negative *bacillus* which was motile, had a polar flagellum, was aerobic and had a salt requirement.

(2) Growth

Artificial seawater (product name: Jamarin S; Jamarin Laboratory) was prepared. Peptone (Difco) at a concentration of 0.3% (w/v) and yeast extract (Difco) at a concentration of 0.02% (w/v) were added thereto. The pH was then adjusted to 7.8 with 3 M sodium carbonate. Agar (Nacalai Tesque) at a concentration of 1.5% (w/v) was added thereto. The mixture was autoclaved to prepare plates. When the above-mentioned microorganism was inoculated onto the plates, it was demonstrated that:

(i) it grew well at 30 to 40° C.;
(ii) the agar gel was liquefied as the cells grew; and
(iii) it grew well at pH 6.0 to 8.0.

NAB2-1-1 was deposited on Jan. 10, 2001 (the date of the original deposit) at International Patent Organism Depositary, National Institute of Advanced Industrial Science and Technology, AIST Tsukuba Central 6, 1-1, Higashi 1-chome, Tsukuba-shi, Ibaraki 305-8566, Japan under accession number FERM BP-7855.

Information on the taxonomic position of the above-mentioned microorganism can be obtained by analyzing the nucleotide sequence of the gene encoding 16S ribosomal RNA (16S rRNA). It is known that the nucleotide sequence of 16S rRNA gene is specific for each microbial strain. Specifically, a chromosomal DNA is extracted from the microorganism NAB2-1-1. A PCR is carried out using primers that can be used to amplify a region of the gene or a portion thereof. A nucleotide sequence of the amplified DNA fragment is determined. Homology search utilizing GenBank database is conducted against the determined sequence. Then, microorganisms that have similar nucleotide sequences in the region, i.e., taxonomically close microorganisms, can be known.

A DNA fragment derived from 16S ribosomal RNA gene in the microorganism NAB2-1-1 was amplified according to a method as described in Bulletin of Japanese Society of Microbial Ecology, 10:31-42 (1995). Primers 27f and 1492r described in the literature were used for the PCR (nucleotide sequences of the primers 27f and 1492r are shown in SEQ ID NOS:32 and 33, respectively). The nucleotide sequence of the resulting amplified DNA fragment was analyzed. As a result, the following microorganisms each having the highest homology of about 90% in the above-mentioned region with the microorganism producing the agarase of the present invention were found:

*Pseudoalteromonas* sp. KT0812A

*Aeromonas schubertii*

The agarase of the present invention can be obtained from NAB2-1-1 as well as a spontaneous or artificial mutant of NAB2-1-1, or a microorganism that belongs to the genus to which NAB2-1-1 belongs and is capable of producing the agarase of the present invention.

An artificial mutant can be obtained according to a known method such as radiation, ultraviolet irradiation or treatment with a mutagenic agent.

It is known that homology between nucleotide sequences of 16S rRNA genes of microorganisms belonging to the same genus is generally about 99% or more. Thus, a microorganism of which the nucleotide sequence of 16S rRNA gene has homology of 99% or more to that of the microorganism NAB2-1-1 can be used like the microorganism NAB2-1-1 according to the present invention.

A medium containing a nitrogen source, an inorganic substance and the like that can be utilized by the microorganism as well as agar, agarose or the like as a carbon source can be used as a medium for culturing the microorganism. Commercially available agar or agarose can be used. Examples of nitrogen sources include meat extract, yeast extract, casein hydrolysate, tryptone and peptone. Yeast extract and peptone are preferably used. Such a nitrogen source can also be used as a carbon source in addition to agar or agarose. Furthermore, sodium chloride, iron citrate, magnesium chloride, sodium sulfate, calcium chloride, potassium chloride, sodium carbonate, sodium bicarbonate, potassium bromide, strontium chloride, sodium borate, sodium silicate, sodium fluoride, ammonium nitrate, disodium hydrogenphosphate and the like can be used in combination as salts.

In particular, a medium prepared by adding peptone, yeast extract and agar or agarose to a medium consisting of artificial seawater Jamarin S can be preferably used. It is preferable to add agar or agarose at a concentration of 0.1 to 2.0%. A solid or liquid medium can be prepared by appropriately changing the concentration of agar or agarose. Liquid culture using a concentration of 0.1 to 0.3% is preferable for the purpose of production of enzyme, whereas solid culture using a concentration of 1.2 to 2.0% is preferable for the purpose of preservation of cells. If low melting point agarose is used for liquid culture, it can be used at a concentration of 0.1 to 1.0%.

For example, the cultivation temperature is 30 to 40° C., the pH of the medium is 6.0 to 8.0, and the cultivation time is 12 to 48 hours, although culture conditions may vary more or less depending on the composition of the medium.

The α-agarase and/or the β-agarase of the present invention produced during cultivation as described above is secreted outside the cells. Then, the cells are removed after cultivation by means of centrifugation, filtration or the like to obtain a culture supernatant.

The resulting culture supernatant can be concentrated using vacuum concentration or ultrafiltration to prepare a liquid enzyme. Alternatively, the culture supernatant can be converted to a powdery enzyme by lyophilization, spray-drying or the like to prepare a crude enzyme preparation. The α-agarase and/or the β-agarase of the present invention can be partially purified by a conventional purification method such as salting out with ammonium sulfate or solvent precipitation. Furthermore, a purified enzyme preparation which results in a single band upon electrophoresis can be obtained using known purification procedures such as column chromatographies (e.g., anion-exchange column and gel filtration column) in combination.

Agarooligosaccharides such as agarobiose, agarotetraose and agarohexaose can be produced by reacting the thus obtained culture or the α-agarase of the present invention in a varying degree of purification with a polysaccharide contained in red algae (e.g., agar or agarose) as a substrate.

Agarose is a polysaccharide that has a structure in which D-galactose and 3,6-anhydro-L-galactose are alternately linked together through α-1,3 bonds and β-1,4 bonds. A β-agarase is an enzyme that hydrolyzes β-1,4 bonds in agarose. Oligosaccharides having D-galactose at their reducing ends generated by the action of this enzyme are called neoagarooligosaccharides, which do not exhibit physiological activities such as those observed for agarooligosaccharides. If an α-agarase which cleaves α-1,3 bonds in agarose is used, agarooligosaccharides having 3,6-anhydro-L-galactose at their reducing ends can be produced. Two enzymes derived from *Alteromonas agarlyticus* GJ1B and a bacterium of genus *Vibrio* (strain JT0107-L4) are known as α-agarases. However, the α-agarase produced by *Alteromonas agarlyticus* GJ1B cannot act on agarohexaose or shorter oligosaccharides, whereas the α-agarase derived from the bacterium of genus *Vibrio* cannot digest agarose. Thus, it was impossible to efficiently produce agarobiose or agarotetraose from agarose a raw material using such an α-agarase.

The α-agarases previously found by the present inventors as described in WO 00/50578 are enzymes that act on agarose, agarohexaose and agarooligosaccharides longer than agarohexaose. Thus, they act on agarose to produce agarooligosaccharides. Furthermore, they can cleave the single α-1,3 bond in agarohexaose generated as a result of the action. Using the enzymes, it is possible to produce agarobiose and agarotetraose, a disaccharide and a tetrasaccharide which have been scarcely produced according to conventional methods. The optimal reaction temperatures of these enzymes are about 40° C. Agarose is often used at a concentration of 1% (w/v). At the concentration, it is not solidified at 50° C., but is solidified at 40° C. That is, if a conventional enzyme is used, agarose at a high concentration is solidified at the optimal reaction temperature for the enzyme, and the enzymatic reaction may be prevented. Therefore, it was difficult to efficiently produce agarobiose or agarotetraose.

On the other hand, since the optimal reaction temperature of the α-agarase of the present invention is 50° C., it can be used for a reaction at a temperature at which agarose is not solidified. Thus, it enables efficient production of agarooligosaccharides.

The α-agarase of the present invention is an enzyme that acts on agarose, agarohexaose and agarooligosaccharides longer than agarohexaose as seen from the above-mentioned physical and chemical properties. Thus, it acts on agarose to produce agarooligosaccharides. Furthermore, it can cleave α-1,3 bonds in agarooligosaccharides, which are generated as a result of the action, to generate smaller agarooligosaccharides such as agarobiose and agarotetraose. In addition, its optimal temperature is high and it is excellently thermostable. Thus, using the α-agarase of the present invention, it is possible to obtain agarobiose and agarotetraose, a disaccharide and a tetrasaccharide which have been difficult to be produced according to conventional methods, in large quantities without prevention of reaction due to solidification of agarose.

Substrate specificities of the conventional α-agarases and the α-agarase of the present invention are shown in Table 1. In the table, the marks + and − represent the ability and inability of the enzyme to digest the substrate, respectively.

TABLE 1

| | Substrate | | |
|---|---|---|---|
| | Agarose | Agarohexaose | Agarotetraose |
| *Alteromonas agarlyticus* GJ1B | + | − | − |
| Bacterium of genus *Vibrio* (JT0107-L4) | − | + | + |
| Agarase 1-7 and Agarase 4-3 | + | + | − |
| Agarase II | + | + | − |

The agarooligosaccharides produced using the α-agarase of the present invention contain agarobiose and agarotetraose. The agarooligosaccharides may contain agarohexaose or agarooligosaccharides longer than agarohexaose as long as the existence does not interfere with the purpose of use. For example, agar, agarose, or oligosaccharides derived from agar or agarose may be used as a raw material for the production of agarobiose, agarotetraose and agarohexaose using the α-agarase of the present invention. The conditions used for the action of the α-agarase are not specifically limited as long as the enzyme exhibits its activity under the conditions used. For example, it is preferable to allow Agarase II to at pH 6.0 to 8.0, at 45 to 55° C. The composition of the reaction mixture is not specifically limited as long as it is suitable for the action of the enzyme.

As described above, the oligosaccharides produced using the α-agarase of the present invention are mainly hexasaccharides or shorter oligosaccharides with low degrees of polymerization. However, it is possible to optionally produce oligosaccharides with different degrees of polymerization by appropriately selecting the reaction conditions or the like. It is also possible to obtain agarobiose, agarotetraose and agarohexaose independently by separating and purifying the thus obtained oligosaccharides.

Agar or agarose can be digested into agarooligosaccharides such as neoagarobiose, neoagarotetraose and neoagarohexaose by allowing the culture or the β-agarase of the present invention in a varying degree of purification obtained as described above to act on a polysaccharide contained in red algae (e.g., agar or agarose).

Enzymes derived from *Vibrio* sp. JT0107-1,4 (JP-A 8-38172) and *Pseudomonas altantica* (Morrice, L. M. et al., Eur. J. Biochem., 135, 553-558 (1983)) are known as β-agarases. The optimal reaction temperatures thereof are about 30° C. If such an enzyme is to be used for extraction of a nucleic acid or the like from an agarose gel, the reaction is prevented because agarose is solidified at a temperature at which the enzyme exhibits its activity. Thus, it cannot be practically used. Enzymes derived from *Flavobacterium* sp. strain NR19 (U.S. Pat. No. 5,869,310), *Pseudomonas* sp. N-7 (JP-B 7-97987) and *Vibrio* sp. PO-303 (JP-A 8-294389) are known to have optimal reaction temperatures higher than the above-mentioned enzymes. However, since their optimal temperatures (55° C. or below) are lower than the melting point of a low melting point agarose gel (65° C.), there remains problems concerning the practical use.

On the other hand, the β-agarase of the present invention exhibits a high activity at wide range of temperatures (50° C. to 70° C.), and it exhibits the maximal activity at 55° C. to 65° C. Therefore, it enables a reaction in which an agarose gel is fully melted. Furthermore, 98% of the activity of the β-agarase of the present invention remains after treatment at 65° C. for 30 minutes, indicating that it is excellently thermostable. Thus, use of the β-agarase of the present invention enables efficient extraction of a nucleic acid or the like from an agarose gel without prevention due to solidification of agarose. Such extraction is difficult according to a conventional method.

The α-agarase gene of the present invention is a gene that encodes a polypeptide having the above-mentioned α-agarase activity. Thus, it refers to a nucleic acid that contains a nucleotide sequence encoding an amino acid sequence for a polypeptide having an α-agarase activity. Examples of the α-agarase genes of the present invention include a gene that contains a nucleotide sequence encoding Agarase II derived from the microorganism NAB2-1-1 (FERM BP-7855). Genes encoding Agarase II are exemplified by a gene having a nucleotide sequence encoding a polypeptide consisting of 772 amino acid residues from amino acid number 318 to amino acid number 1089 in SEQ ID NO:23.

The α-agarase genes of the present invention also include a nucleic acid that contains a nucleotide sequence encoding a polypeptide that has an amino acid sequence in which one or more amino acids are substituted, deleted, added or inserted in the above-mentioned amino acid sequence and has an α-agarase activity.

Also, the genes of the present invention include a gene having a nucleotide sequence consisting of 2316 nucleotides from nucleotide number 952 to nucleotide number 3267 in SEQ ID NO:21. The genes of the present invention also include a nucleic acid containing a nucleotide sequence that has a nucleotide sequence in which one or more nucleotides are substituted, deleted, added or inserted in the above-mentioned nucleotide sequence and encodes a polypeptide having an α-agarase activity.

Furthermore, the genes of the present invention include a nucleic acid containing a nucleotide sequence that hybridizes to the above-mentioned gene under stringent conditions and encodes a polypeptide having an α-agarase activity. Hybridization can be carried out according to a method as described in, for example, T. Maniatis et al. (eds.), Molecular Cloning: A Laboratory Manual 2nd ed., 1989, Cold Spring Harbor Laboratory. The stringent conditions are exemplified by incubation with a probe at 65° C. overnight in a solution containing 6×SSC (1×SSC: 0.15 M sodium chloride, 0.015 M sodium citrate, pH 7.0), 0.5% SDS, 5×Denhardt's and 100 mg/ml of herring sperm DNA.

The β-agarase gene of the present invention is a gene that encodes a polypeptide having the above-mentioned β-agarase activity. Thus, it refers to a nucleic acid that contains a nucleotide sequence encoding an amino acid sequence for a polypeptide having a β-agarase activity. Examples of the β-agarase genes of the present invention include a gene that contains a nucleotide sequence encoding Agarase I derived from the microorganism NAB2-1-1 (FERM BP-7855). Genes encoding Agarase I are exemplified by a gene having a nucleotide sequence encoding a polypeptide consisting of 417 amino acid residues from amino acid number 21 to amino acid number 437 in SEQ ID NO:22.

The β-agarase genes of the present invention also include a nucleic acid that contains a nucleotide sequence encoding a polypeptide that has an amino acid sequence in which one or more amino acids are substituted, deleted, added or inserted in the above-mentioned amino acid sequence and has a β-agarase activity.

Also, the genes of the present invention include a gene having a nucleotide sequence consisting of 1251 nucleotides from nucleotide number 61 to nucleotide number 1311 in SEQ ID NO:20. The genes of the present invention also include a nucleic acid containing a nucleotide sequence that has a nucleotide sequence in which one or more nucleotides are substituted, deleted, added or inserted in the above-mentioned nucleotide sequence and encodes a polypeptide having a β-agarase activity.

Furthermore, the genes of the present invention include a nucleic acid containing a nucleotide sequence that hybridizes to the above-mentioned gene under stringent conditions and encodes a polypeptide having a β-agarase activity. The stringent conditions are exemplified by those as described above.

For example, the agarase gene of the present invention can be cloned as follows.

A genomic DNA is prepared from a microorganism producing an agarase. The genomic DNA can be prepared according to an appropriate known method. For example, it can be prepared using known procedures such as lysozyme treatment, protease treatment, RNase treatment, phenol treatment and ethanol precipitation in combination. The thus obtained genomic DNA is degraded by appropriate known means such as sonication or digestion with a restriction enzyme. The resulting DNA fragments are incorporated into a vector (e.g., a plasmid vector) according to a conventional method to construct recombinant DNA molecules. The recombinant DNA molecules are then introduced into an appropriate host (e.g., *Escherichia coli*) to obtain transformants. Procedures for construction of recombinant DNA molecules, transformation and the like suitable for the vector and the host to be used can be selected from conventional methods, for example, those described in Molecular Cloning: A Laboratory Manual 2nd ed. Thus, a genomic library that contains a transformant harboring an agarase gene is obtained.

Next, the genomic library is screened to select the transformant harboring the agarase gene. The agarase gene can be isolated from the transformant. Examples of screening methods are as follows.

(1) Screening Using Expression of Agarase Activity as Index

A genomic library is grown on agar plates. A transformant harboring an agarase gene expresses a polypeptide having an agarase activity. The polypeptide lyses an agar gel by the action of its agarase activity. Accordingly, a colony or a plaque that lyses an agar gel in an agar plate is selected.

(2) Screening Using Antibody

A crude, partially purified or purified enzyme preparation of an agarase is prepared as described above. An anti-agarase antibody is prepared using the preparation as an antigen according to a conventional method.

A genomic library is grown on plates. Grown colonies or plaques are transferred onto nylon or nitrocellulose filters. Expressed recombinant proteins are transferred onto the filters along with the colonies or plaques. The recombinant proteins on the filters are reacted with the anti-agarase antibody to identify a clone reactive with the antibody.

The clone reactive with the antibody can be identified according to a known method, for example, by reacting a peroxidase-conjugated secondary antibody with the filters which have been reacted with the anti-agarase antibody, incubating the filter with a chromogenic substrate and then detecting developed color.

If an expression vector that results in high expression of a gene in a DNA incorporated in the vector is used for the construction of the genomic library to be used in the method (1) or (2) as described above, a transformant harboring the gene of interest can be readily selected.

(3) Screening by Hybridization Using DNA Probe

A genomic library is grown on plates. Grown colonies or plaques are transferred onto nylon or nitrocellulose filters. DNAs are immobilized onto the filters by denaturation. The DNAs on the filters are hybridized to a labeled probe according to a conventional method to identify a clone that hybridizes to the probe.

Probes used for this screening include an oligonucleotide prepared on the basis of information on the above-mentioned amino acid sequence of the agarase, an oligonucleotide prepared on the basis of information on another amino acid sequence, and a PCR fragment amplified using primers prepared on the basis of information on such an amino acid sequence. Examples of labels used for the probes include, but are not limited to, a radioisotopic label, a fluorescent label, a digoxigenin label and a biotin label.

A genomic library enriched for transformants harboring an agarase gene prepared as follows may be used as a genomic library to be used for the screening.

A genomic DNA is prepared from a microorganism producing an agarase, digested with an appropriate restriction enzyme, separated by agarose gel electrophoresis and then blotted onto a nylon or nitrocellulose filter according to a conventional method. The DNAs on the filter are hybridized to the above-mentioned labeled probe according to a conventional method to detect a DNA fragment that hybridizes to the probe. DNA fragments corresponding to the signal are extracted and purified from the agarose gel.

The thus obtained DNA fragments are incorporated into a vector (e.g., a plasmid vector) according to a conventional method to construct recombinant DNA molecules. The recombinant DNA molecules are then introduced into an appropriate host (e.g., *Escherichia coli*) to obtain transformants. A transformation method suitable for the vector to be used can be selected from conventional methods, for example, those described in Molecular Cloning: A Laboratory Manual 2nd ed. Thus, a genomic library enriched for transformants harboring an agarase gene is obtained.

A screening can be carried out more efficiently by using such a genomic library.

The gene of interest is cloned by screening transformants in the methods (1) to (3) as described above. By using a PCR, cloning can be carried out in vitro without utilizing transformants.

A genomic DNA is prepared from a microorganism producing an agarase. A PCR is carried out using the genomic DNA as a template and a pair of primers prepared on the basis of information on the amino acid sequence of the agarase. Thus, a DNA fragment containing an agarase gene can be obtained. Furthermore, the full-length agarase gene can be obtained, for example, by hybridization using the fragment as a probe, or a PCR using primers prepared based on the nucleotide sequence of the fragment. The nucleotide sequence of the gene obtained as described above can be determined according to a known method. If the clone does not encode the entire agarase polypeptide, the entire open reading frame (ORF) for the agarase is revealed by repeating a procedure comprising preparation of a new probe based on the determined nucleotide sequence and screening of a genomic library using the probe to obtain a new clone. A clone that contains the entire ORF encoding the agarase can be made based on the thus obtained information, for example.

A polypeptide having an agarase activity can be produced in large quantities by genetic engineering by connecting the gene encoding the agarase obtained as described above with an appropriate expression vector.

A method for obtaining the gene of the present invention is described below in brief.

Cells obtained by culturing the microorganism NAB2-1-1 are lysed using lysozyme, and then subjected to removal of proteins, ethanol precipitation and the like to obtain a chromosomal DNA. The NAB2-1-1 chromosomal DNA is completely digested with a restriction enzyme. An adaptor corresponding to the restriction enzyme is ligated to the digested DNA. A PCR is carried out using the resulting chromosomal DNA as a template as well as a primer prepared on the basis of the N-terminal or internal amino acid sequence of Agarase I or II of the present invention and a primer corresponding to the nucleotide sequence of the adaptor.

A nucleotide sequence that encodes the agarase of the present invention can be determined by analyzing the nucleotide sequence of the PCR product obtained as described above. If the entire sequence cannot be determined, the above-mentioned procedure may be repeated. Alternatively, primer waking may be carried out using the chromosomal DNA as a template.

The primer designed on the basis of the amino acid sequence of the agarase may be a mixed primer. Alternatively, it may be possible to use new primers prepared based on a nucleotide sequence of an amplification product obtained by a PCR using primers prepared on the basis of the N-terminal and internal amino acid sequences and the NAB2-1-1 chromosomal DNA as a template.

The thus obtained gene encoding Agarase II has an ORF that encodes a polypeptide consisting of 1089 amino acids. The nucleotide sequence of the ORF is shown in SEQ ID NO:21. The amino acid sequence encoded by the nucleotide sequence of the ORF is shown in SEQ ID NO:23. A nucleotide sequence corresponding to P2 (the N-terminal amino acid sequence of Agarase II), an upstream nucleotide sequence encoding 26 amino acids having a signal peptide-like sequence, and an SD-like sequence in a further upstream region are found in the nucleotide sequence of the gene.

Thus, the amino acid sequence of SEQ ID NO:23 is an example of the α-agarase of the present invention. Comparison of this amino acid sequence with the previously determined N-terminal amino acid sequence of Agarase II shows that Agarase II is a polypeptide consisting of an amino acid sequence from amino acid number 27 to amino acid number 1089 in the amino acid sequence of SEQ ID NO:23, and that the amino acid sequence is encoded by a nucleotide sequence from nucleotide number 79 to nucleotide number 3270 (including the termination codon) in the nucleotide sequence of SEQ ID NO:21.

Three putative Ca-binding regions (171-184, 271-283 and 987-999) are found in the ORF.

The gene encoding Agarase I has an ORF that encode a polypeptide consisting of 438 amino acids. The nucleotide sequence of the ORF is shown in SEQ ID NO:20. The amino acid sequence encoded by the nucleotide sequence of the ORF is shown in SEQ ID NO:22. A nucleotide sequence corresponding to P1 (the N-terminal amino acid sequence of Agarase I), an upstream nucleotide sequence encoding 20 amino acids, and an SD-like sequence in a further upstream region are found in the nucleotide sequence of the gene.

Thus, the amino acid sequence of SEQ ID NO:22 is an example of the agarase of the present invention. Comparison of this amino acid sequence with the previously determined N-terminal amino acid sequence of Agarase I shows that Agarase I is a polypeptide consisting of an amino acid sequence from amino acid number 21 to amino acid number 438 in the amino acid sequence of SEQ ID NO:22, and that the amino acid sequence is encoded by a nucleotide sequence from nucleotide number 61 to nucleotide number 1314 (including the termination codon) in the nucleotide sequence of SEQ ID NO:20.

The amino acid sequence of Agarase I obtained as described above has only 33% homology to an amino acid sequence of a known β-agarase from *Flavobacterium* sp. strain NR19. Thus, it is considered that Agarase I of the present invention has an absolutely novel sequence.

A recombinant DNA molecule can be constructed by connecting a gene encoding the agarase of the present invention (e.g., the gene encoding Agarase I or Agarase II) to an appropriate vector. Furthermore, a transformant can be made by introducing the recombinant DNA molecule into an appropriate host. The agarase of the present invention is produced in a culture obtained by culturing the transformant. Thus, it is possible to produce the agarase of the present invention (e.g., Agarase I or Agarase II) in large quantities using the transformant.

A mutated agarase can be produced by introducing a mutation into a gene encoding an agarase according to a known method. Examples of the methods for introducing a mutation that can be used include, but are not limited to, the oligonucleotide double amber method (Hashimoto-Gotoh, T. et al., Gene, 152:271-275 (1995)), the gapped duplex method (Kramer, W. et al., Nucl. Acids Res., 12:9441 (1984); Kramer, W. et al., Methods in Enzymology, 154:350 (1987)) and the Kunkel method (Kunkel, T. A., Proc. Natl. Acad. Sci. USA, 82:488 (1985); Kunkel, T. A., Methods in Enzymology, 154: 367 (1987)).

The agarase of interest can be secreted outside a transformant by expressing a gene that encodes a polypeptide in which a signal sequence is added at the N-terminus of an agarase to be expressed. The signal sequence is not limited to specific one, and exemplified by the signal sequence for Agarase I represented by amino acid number 1 to amino acid number 20 in SEQ ID NO:22. This signal sequence is encoded by a nucleotide sequence from nucleotide number 1 to nucleotide number 60 in SEQ ID NO:20. Alternatively, the signal sequence is exemplified by the signal sequence for Agarase II represented by amino acid number 1 to amino acid number 26 in SEQ ID NO:23. This signal sequence is encoded by a nucleotide sequence from nucleotide number 1 to nucleotide number 78 in SEQ ID NO:21.

Examples of vectors that can be used for constructing the recombinant DNA molecules include, but are not limited to, plasmid vectors, phage vectors and virus vectors. An appropriate vector may be selected depending on the purpose for which the recombinant DNA is used. If a recombinant DNA molecule is constructed in order to produce an agarase, a vector that contains a promoter and/or other regions for expression control is preferable. Examples of such plasmid vectors include, but are not limited to, pKF19k, pT7BlueT and pET16b. Hosts that can be used for making transformants include, but are not limited to, microorganisms such as bacteria, yeasts and filamentous fungi, as well as cultured cells of mammals, fishes, insects and the like. A recombinant DNA molecule constructed using a vector suitable for the host is used for making a transformant.

A method for producing Agarase I by genetic engineering is described below in brief.

A DNA fragment containing a nucleotide sequence that encodes a polypeptide having, for example, an amino acid sequence starting from amino acid number 21 in SEQ ID NO:22 is inserted into an appropriate plasmid vector (e.g., pKF19k (Takara Shuzo), pT7BlueT (Takara Shuzo) or pET16b (Takara Shuzo)) to construct a plasmid. *Escherichia coli* (e.g., *Escherichia coli* JM109 or BL21(DE3)pLysS) transformed with such a plasmid is cultured in an appropriate liquid medium. Induction is carried out using IPTG or the like, if necessary. The polypeptide encoded by the DNA fragment inserted in the plasmid is expressed. The β-agarase activity expressed by such a transformant in a unit volume of culture is usually higher than that observed for a culture of NAB2-1-1.

For Agarase II, a transformant expressing Agarase II can be made by genetic engineering as described above for Agarase I using a DNA fragment containing a nucleotide sequence that encodes a polypeptide having, for example, an amino acid sequence starting from amino acid number 27, 181 or 318 in SEQ ID NO:23. The resulting transformant expresses an α-agarase activity, and the activity in a unit volume of culture is usually higher than that observed for a culture of NAB2-1-1.

The agarase of the present invention produced by genetic engineering as described above can be partially purified by a conventional purification method such as salting out with ammonium sulfate or solvent precipitation. Furthermore, a purified enzyme preparation which results in a single band upon electrophoresis can be obtained using known purification procedures such as column chromatographies (e.g., anion-exchange column and gel filtration column) in combination.

If the agarase of the present invention produced by genetic engineering is insolubilized, it can be solubilized according to a known method and recovered.

Agarooligosaccharides such as agarobiose, agarotetraose, agarohexaose and agarooctaose can be produced by reacting the thus obtained recombinant α-agarase of the present invention in a varying degree of purification with a polysaccharide contained in red algae (e.g., agar or agarose) as a substrate.

For example, the agarooligosaccharides can be produced by a reaction at 50° C. for 16 hours using 1% (w/v) agarose as a substrate.

Similarly, a material (e.g., a nucleic acid) in an agarose gel can be efficiently extracted by allowing the thus obtained recombinant β-agarase of the present invention in a varying degree of purification to act on an agarose gel which has been subjected to electrophoresis of a nucleic acid or the like.

For example, in case of electrophoresis on a 1% (w/v) or 3% (w/v) agarose gel, a material in the gel can be efficiently extracted by allowing the recombinant β-agarase of the present invention to act on the agarose gel containing the material of interest at 67° C. for 10 minutes.

Thermostability of the agarase of the present invention can be improved by deleting up to 30% of the ORF from the N terminus. The region to be deleted is not specifically limited as long as it is up to 30% (e.g., 10%, 20%, etc.) of the ORF.

For example, the thermostability of Agarase II can be improved by deleting 29.1% (i.e., 317 amino acids) of Agarase II from the N terminus. A particularly marked improvement in the thermostability is observed in the presence of calcium.

There is no specific limitation concerning the method for deleting an N-terminal portion for improving thermostability. It may be carried out by treatment with a protease or by using genetic engineering techniques.

EXAMPLES

The following Examples illustrate the present invention in more detail, but are not to be construed to limit the scope thereof.

Example 1

Method for Measuring Activity

Upon purification of the agarase of the present invention, the activity of the purified or partially purified preparation of the enzyme was measured by conducting an enzymatic reaction using Agarose LO3 (Takara Shuzo) as a substrate and then quantifying the resulting agarotetraose or neoagarotetraose using high performance liquid chromatography. The procedure is described in detail below.

A solution containing agarose at a concentration of 0.2% (w/v) or 0.5% (w/v) in 20 mM Tris-HCl buffer (pH 7.2) containing 10 mM sodium chloride (in case of Agarase I) or 20 mM Tris-HCl buffer (pH 7.2) containing 10 mM calcium chloride and 10 mM sodium chloride (in case of Agarase II) was prepared. 180 μl of this solution as a substrate was mixed with 20 μl of an enzyme solution. The mixture was reacted at 50° C. for 5 to 30 minutes, preferably 10 minutes, and then heated in boiling water or at 75° C. for 1 minute to stop the reaction. 30 μl of the reaction mixture was subjected to a TSKgel α-2500 column (inner diameter: 7.8 mm; length: 300 mm; Tosoh). Elution was carried out using a 70% acetonitrile solution as an eluent at a flow rate of 0.8 ml/minute. Agarotetraose eluted at a retention time of about 25 minutes or neoagarotetraose eluted at a retention time of about 24 minutes, which was generated by the enzymatic reaction, was quantified. One unit (1 U) is defined as the amount of the enzyme that produces 1 μmol of agarotetraose or neoagarotetraose in 10 minutes.

Example 2

Production of Agarase from NAB2-1-1

100 ml of artificial seawater (product name: Jamarin S; Jamarin Laboratory) was prepared. Peptone (Difco) and yeast extract (Difco) were added thereto at concentrations of 0.3% (w/v) and 0.02% (w/v), respectively. The pH was then adjusted to 7.8 using 3 M sodium carbonate. The resulting mixture was transferred into a 500-ml Erlenmeyer flask. 0.4 g of NuSieve GTG Agarose (Takara Shuzo) was added thereto. After sterilization using an autoclave, NAB2-1-1 was inoculated into the mixture, and cultured at 37° C. at 120 rpm overnight. The resulting culture was used as a preculture.

The main cultivation was conducted as follows. 3,000 ml of artificial seawater (product name: Jamarin S; Jamarin Laboratory) was prepared in a 5,000-ml jar fermentor vessel. Peptone (Difco) and yeast extract (Difco) were added thereto at concentrations of 0.3% (w/v) and 0.02% (w/v), respectively. The pH was then adjusted to 7.8. 12 g of NuSieve GTG Agarose (Takara Shuzo) was added thereto. The mixture was sterilized using an autoclave. 30 ml of the preculture was inoculated into the mixture and cultured at 37° C. at 250 rpm for 18 hours. The culture was then centrifuged at 8,000×g for 20 minutes to collect about 3,000 ml of a supernatant from which cells had been removed.

The following procedures were carried out at 4° C. or below.

The supernatant was placed in a dialysis membrane (Sanko Junyaku) and soaked in about 500 g of polyethylene glycol over two nights to concentrate it about 10-fold. 300 ml of the concentrate was dialyzed against Buffer I (20 mM Tris-HCl buffer (pH 7.2) containing 10 mM calcium chloride and 10 mM sodium chloride) for desalting.

The dialysate was loaded onto a column (φ 2.0 cm×12 cm) filled with anion-exchange resin DEAE Toyopearl 650M (Tosoh) which had been equilibrated with the buffer. The column was washed with about 120 ml of Buffer I. The non-adsorptive fraction and the washing fraction (about 400 ml) were collected and combined as an Agarase I fraction. Elution was carried out using a linear gradient of 10 mM to 1,000 mM sodium chloride (total elution volume: 400 ml). A fraction of about 160 ml eluted at a sodium chloride concentration between 300 mM and 600 mM was collected as an Agarase II fraction.

The Agarase I fraction and the Agarase II fraction were dialyzed against Buffer II (20 mM Tris-HCl buffer (pH 7.2) containing 10 mM calcium chloride, 10 mM sodium chloride, 5% glycerol and 1 mM PMSF) for desalting.

The Agarase II fraction was subjected to further purification as follows. The dialyzed Agarase II fraction was loaded onto a column (φ 2.0 cm×8.0 cm) filled with 25 ml of QAE Toyopearl 550C (Tosoh). In this case, elution was carried out using a linear gradient of 10 mM to 800 mM sodium chloride (total elution volume: 250 ml). A fraction of about 70 ml eluted at about 500 mM was obtained. This fraction was dialyzed against Buffer II, and concentrated to a volume of about 1 ml using a centrifugation ultrafiltration membrane CENTRIPREP-10 (Amicon). The concentrate was subjected to gel filtration using a column (φ 0.8 cm×50 cm) filled with Sephadex G-100 (Pharmacia) equilibrated with Buffer II. An Agarase II fraction of about 20 ml was obtained. This fraction was concentrated to a volume of about 1 ml using an ultrafiltration membrane again.

Electrophoresis of the purified protein on a polyacrylamide gel containing sodium dodecyl sulfate (SDS) revealed that it was purified almost to homogeneity. The total activity was about 150 U.

The Agarase I fraction was subjected to further purification as follows.

The dialyzed Agarase I fraction (about 400 ml) was adsorbed to a column (φ 2.0 cm×9.5 cm) filled with CM Toyopearl 650 (Tosoh) which had been equilibrated with Buffer II. Elution was carried out using a linear gradient of 10 mM to 1,000 mM sodium chloride (total elution volume: 300 ml). An Agarase I fraction of about 90 ml eluted at a sodium chloride concentration up to 300 mM was collected. This fraction was dialyzed overnight against Buffer II containing 1.0 M ammonium sulfate, and loaded onto a column (φ 2.0 cm×9.5 cm) filled with 30 ml of Butyl Toyopearl 650M (Tosoh) equilibrated with the same buffer. Elution was carried out using a gradient of 1.0 M to 0 M ammonium sulfate (total elution volume: 300 ml). An Agarase I fraction (about 60 ml) eluted at concentrations ranging from 300 mM to 0 M was recovered. Like Agarase II, the fraction was dialyzed against Buffer II and concentrated to a volume of about 1 ml using a centrifugation ultrafiltration membrane CENTRIPREP-10 (Amicon).

Electrophoresis of the purified protein on a polyacrylamide gel containing sodium dodecyl sulfate (SDS) revealed that it was purified almost to homogeneity. The total activity was about 310 U.

Example 3

Examination of Various Properties of Enzymes

[Identification of Products of Reactions with Agarase I and Agarase II]
20 µl of a solution containing agarose at a concentration of 0.5% (w/v) in 20 mM Tris-HCl buffer (pH 7.2) containing 10 mM sodium chloride (in case of Agarase I) or 20 mM Tris-HCl buffer (pH 7.2) containing 10 mM calcium chloride and 10 mM sodium chloride (in case of Agarase II) was subjected to digestion using the purified enzyme of Agarase I or Agarase II. The digestion product was subjected to a gel filtration column (Tosoh, TSKgel α-2500) using 70% acetonitrile as an eluent. As a result, main peaks were observed at about 24 minutes and about 28 minutes for Agarase I. It was considered that these peaks correspond to neoagarotetraose and neoagarohexaose, respectively, based on the retention times observed for standards. For the digestion product with Agarase II, main peaks were observed at retention times of about 22 minutes, about 25 minutes and about 29 minutes. It was considered that these peaks correspond to agarobiose, agarotetraose and agarohexaose, respectively, based on the retention times observed for standards. The reaction product was confirmed by subjecting it to thin layer chromatography using a developing solvent having a composition of chloroform: methanol acetic acid=3:3:1 with two rounds of development. Three agarooligosaccharides, i.e., agarobiose (Rf value=0.76), agarotetraose (Rf value=0.50) and agarohexaose (Rf value=0.33), as well as two neoagarooligosaccharides, i.e., neoagarotetraose (Rf value=0.59) and neoagarohexaose (Rf value=0.41), were used as controls. As a result, color-developing substances were observed using orcinol-sulfuric acid at positions corresponding to neoagarooligosaccharides for the reaction product obtained using Agarase I. Color-developing substances were observed at positions corresponding to agarooligosaccharides for the reaction product obtained using Agarase II. These results show that Agarase I is a β-agarase that hydrolyzes a β-1,4 bond between D-galactose and 3,6-anhydro-L-galactose in an agarose molecule to produce neoagarooligosaccharides, whereas Agarase II is an α-agarase that hydrolyzes an α-1,3 bond in an agarose molecule to produce agarooligosaccharides.

[Ca Ion Requirement]
The Agarase I solution and the Agarase II solution were dialyzed against a calcium-free buffer (20 mM Tris-HCl buffer (pH 7.2) containing 10 mM sodium chloride and 1 mM EDTA) overnight. A solution containing agarose at a concentration of 0.2% (w/v) in 20 mM Tris-HCl buffer (pH 7.2) containing 10 mM sodium chloride and 1 mM EDTA was added thereto. The mixture was reacted at 50° C. for 10 minutes. The reaction was stopped by heating in boiling water for 1 minute (in case of Agarase I) or at 75° C. for 1 minute (in case of Agarase II). Then, the activities were measured. The activity observed when the reaction was carried out using a conventional buffer containing calcium was defined as 100%. As a result, Agarase I and Agarase II exhibited about 100% and about 60% of their activities, respectively.

[Optimal Temperature]
The temperatures at which inactivation of the enzymes was suppressed and the reactions rapidly proceeded for Agarase I and Agarase II were 50 to 65° C. and 45 to 55° C., respectively.

[Thermostability]
The enzyme solution was heated at 48° C., 50° C., 55° C., 60° C. or 65° C. for a given period. A solution containing agarose at a concentration of 0.2% (w/v) in 20 mM Tris-HCl buffer (pH 7.2) containing 10 mM sodium chloride (in case of Agarase I), or 20 mM Tris-HCl buffer (pH 7.2) containing 10 mM calcium chloride and 10 mM sodium chloride (in case of Agarase II) was then added to the heated solution. The mixture was reacted at 50° C. for 10 minutes. The reaction was stopped by heating in boiling water for 1 minute (in case of Agarase I) or at 75° C. for 1 minute (in case of Agarase II). Then, the activities were measured. The activity observed for a conventional reaction at 50° C. for 10 minutes was defined as 100%. As a result, Agarase I exhibited about 85% of its activity after treatment at 65° C. for 60 minutes, and Agarase II exhibited about 40% of its activity after treatment at 55° C. for 10 minutes.

[Molecular Weight]
The molecular weight was determined using SDS-polyacrylamide gel electrophoresis. The SDS-polyacrylamide gel electrophoresis was carried out according to a conventional method using a 10-20% polyacrylamide gel containing SDS along with a molecular weight marker (Bio-Rad, myosin (MW 200,000), β-galactosidase (MW 116,250) phosphorylase b (MW 97,400), bovine serum albumin (MW 66,200), ovalbumin (MW 45,000), carbonic anhydrase (MW 31,000), trypsin inhibitor (MW 21,500), lysozyme (MW 14,400)). The molecular weights of Agarase I and Agarase II were about 48,000 and about 117,000 as determined based on the mobility, respectively.

[Amino-Terminal Amino Acid Sequence]
The amino-terminal amino acid sequences of Agarase I and Agarase II were determined according to the Edman degradation method. A solution of purified enzyme preparation containing Agarase I or Agarase II corresponding to about 10 pmol of the enzyme protein was subjected to SDS-PAGE using a 10-20% polyacrylamide gradient gel. After electrophoresis, the enzyme separated on the gel was blotted onto a membrane ProBlot (Applied Biosystems). A portion of the membrane to which the enzyme had been adsorbed was analyzed using a protein sequencer G1000A (Hewlett Packard). As a result, the determined amino-terminal amino acid sequences of Agarase I (P1; SEQ ID NO:1) and Agarase II (P2; SEQ ID NO:2) were Ala-Asp-Xaa-Asp-Gly-Val-Pro-Ile-Pro-Ala-Pro-Ala-Gly and Glu-Thr-Ile-Val-Leu-Gln-Ala-Glu-Ser-Phe, respectively.

[Determination of Partial Amino Acid Sequence]
Carboxylmethylation of cysteine residues was carried out using 2 nmol of the purified Agarase I or II. Peptide fragments were separated and purified using HPLC from a digestion product obtained by digestion with lysylendopeptidase. µBondasphare C8 (Waters) was used for the column, and Solution A (0.1% TFA) and Solution B (0.1% TFA containing 80% acetonitrile) were used for elution. Elution was carried out at a flow rate of 0.5 ml/minute by increasing the ratio of Solution B from 0% to 100% in 50 minutes in a linear manner. Detection was carried out at 214 nm for collecting fractions. The respective peptide fractions were subjected to amino acid sequence analyses. For Agarase I, partial amino acid sequences PI3 (SEQ ID NO:3) and PI4 (SEQ ID NO:4) were determined. For Agarase II, partial amino acid sequences PII5 (SEQ ID NO:5), PII6 (SEQ ID NO:6) and PII7 (SEQ ID NO:7) were determined.

Example 4

Production of Agarooligosaccharides

Agarose LO3 was added to 2 ml of a buffer for reaction (20 mM Tris-HCl buffer (pH 7.2) containing 10 mM calcium chloride and 10 mM sodium chloride) at a final concentration of 1.0% (w/v). About 1.0 U of the purified preparation of Agarase II was further added thereto. The mixture was reacted at 50° C. for 16 hours. After reaction, the reaction mixture was filtered through a 0.22-μm filter (Millipore). The filtered reaction mixture was analyzed using high performance liquid chromatography under the same conditions as those used for measuring the activity of the enzyme of the present invention in Example 1 to determine generated agarooligosaccharides. As a result, agarobiose, agarotetraose and agarohexaose were detected in the reaction mixture. Thus, it was confirmed that the above-mentioned enzymatic reaction produces these smaller agarooligosaccharides.

Example 5

Production of Neoagarooligosaccharides

Agarose LO3 was added to 2 ml of a buffer for reaction (20 mM Tris-HCl buffer (pH 7.2) containing 10 mM sodium chloride) at a final concentration of 1.0% (w/v). About 1.0 U of the purified preparation of Agarase I was further added thereto. The mixture was reacted at 65° C. for 16 hours. After reaction, the reaction mixture was filtered through a 0.22-μm filter (Millipore). The filtered reaction mixture was analyzed using high performance liquid chromatography under the same conditions as those used for measuring the activity of the enzyme of the present invention in Example 1 to determine generated neoagarooligosaccharides. As a result, neoagarotetraose and neoagarohexaose were detected in the reaction mixture. Thus, it was confirmed that the above-mentioned enzymatic reaction produces these smaller neoagarooligosaccharides.

Example 6

Recovery of Nucleic Acid from Agarose Gel Using Agarase I

1 μg of a DNA molecular weight marker, —HindIII (Takara Shuzo), was electrophoresed on a 1.0% (w/v) Sea-Plaque GTG Agarose gel. A gel containing separated DNA fragments having sizes of about 4.4 kbp and about 6.6 kbp was excised and placed in a 1.5-ml Eppendorf tube. 1 ml of a reaction buffer (20 mM Tris-HCl buffer (pH 7.2) containing 50 mM sodium chloride) was added thereto. The mixture was allowed to stand at room temperature for 10 minutes. The buffer was then discarded and the gel was left in the tube. The tube was incubated at 67° C. for 5 minutes for melting the gel. 1.0 U of the purified Agarase I enzyme was added thereto. The mixture was incubated at the temperature for 10 minutes. The Eppendorf tube was placed on ice to confirm that the agarose gel was completely dissolved. Ethanol precipitation was then carried out according to a conventional method to recover the DNA fragments. Similarly, a DNA molecular weight marker, 100 bp Ladder Marker (Takara Shuzo), was subjected recovery of DNA from a 3.0% (w/v) NuSieve GTG Agarose gel. In this case, DNA fragments of 400 bp and 500 bp were recovered. Results of comparison of the DNA recovery rates with those for a commercially available β-agarase derived from *Pseudoalteromonas atlantica* (Takara Shuzo) are shown in Table 2.

If the commercially available β-agarase is used, the temperature should be lowered from that used for melting an agarose gel to one at which the enzyme can act before addition of the enzyme. Since the reaction temperature is low, a long reaction time is required and the period required for the procedure is prolonged.

On the other hand, if Agarase I of the present invention is used, the enzyme can be added immediately after melting an agarose gel. Since the reaction can be carried out at a high temperature without lowering the temperature, only a short period is required for the procedure.

TABLE 2

| Marker | Size of recovered DNA fragment | Recovery rate (%)* | |
|---|---|---|---|
| | | Agarase I | β-Agarase (commercially available) |
| λ-HindIII | 4.4 kbp | 78 | 51 |
| | 6.6 kbp | 86 | 55 |
| 100 bp Ladder | 400 bp | 84 | 32 |
| | 500 bp | 81 | 45 |
| Require period** | | ca 30 min | ca 3 hr |

*Amount of recovered DNA/amount of applied DNA × 100.
**Period required until ethanol precipitation.

Example 7

Preparation of Chromosomal DNA from NAB2-1-1

One liter of artificial seawater (product name: Jamarin S; Jamarin Laboratory) was prepared. Peptone (Difco) and yeast extract (Difco) were added thereto at concentrations of 0.3% (w/v) and 0.02% (w/v), respectively. The pH was then adjusted to 7.8 using 3 M sodium carbonate. Agar (Nacalai Tesque) was added thereto at a concentration of 0.1% (w/v). The mixture was sterilized using an autoclave. 10 μl of a glycerol stock of the agarase-producing strain NAB2-1-1 was inoculated into 2 ml of the medium and cultured at 37° C. overnight. 1 ml of the culture was inoculated into 100 ml of the same medium and cultured at 37° C. overnight. The cells were collected by centrifugation at 8,000×g for 10 minutes. The cells were suspended in 10 ml of Buffer A (100 mM Tris-HCl buffer (pH 8.0) containing 100 mM NaCl and 10 mM EDTA (pH 8.0)). 0.25 ml of a lysozyme solution (20 mg/ml) was added thereto. The mixture was incubated at 37° C. for 1 hour. 2.5 ml of Buffer A containing SDS at a concentration of 5.0% was then added thereto. The resulting mixture was incubated at 60° C. for 20 minutes while shaking. 1.5 ml of a protease K solution (20 mg/ml) was added thereto. The mixture was incubated at 37° C. overnight. Almost equal volume of phenol was then added to the mixture, and the resulting mixture was gently shaken at room temperature for about 10 minutes. The mixture was centrifuged at 2,000×g for 10 minutes. The supernatant was transferred into cold ethanol. A chromosomal DNA was wound using a glass bar. Almost equal volume of phenol was added to the solution from which the chromosomal DNA had been wound, and the similar procedure was carried out to wind a chromosomal DNA again. The chromosomal DNA was suspended in 10 μl of Buffer A. 50 μl of an RNase A solution (10 mg/ml) was added thereto, and the mixture was incubated at 37° C. for 10 minutes. The chromosomal DNA was recovered from the solution by ethanol precipitation and suspended in 5 ml of Buffer B (20 mM Tris-HCl buffer (pH 7.5) containing 140 mM NaCl and 1 mM EDTA (pH 7.5)). The suspension was dialyzed against the same buffer overnight. Then, about 5.0 mg of the chromosomal DNA was obtained. The purity of the DNA was examined based on OD260 nm/280 nm. The value was about 1.8 in each case. The chromosomal DNA was used for cloning of Agarase I and Agarase II as described below.

Example 8

Cloning of Agarase I Gene

Mixed primers 1 and 2 (SEQ ID NOS:8 and 9) were designed on the basis of the N-terminal amino acid sequence of Agarase I, P1 (SEQ ID NO:1) determined as described in Example 3, synthesized using a DNA synthesizer and purified. Specifically, the mixed primers 1 and 2 represented by SEQ ID NOS:8 and 9 correspond to amino acid sequences of amino acid numbers 4-10 and 4-13 in the amino acid sequence P1, respectively. Cloning of the Agarase I gene was carried out using these primers and LA PCR in vitro cloning kit (Takara Shuzo).

A primary PCR was carried out as follows. The chromosomal DNA prepared in Example 7 was completely digested with a restriction enzyme BamHI. A BamHI adaptor was ligated to the termini of the digested DNA using DNA Ligation Kit (Takara Shuzo). A portion thereof was placed in a 0.5-ml tube for PCR. 5 μl of 10×LA PCR buffer, 8 μl of a dNTP mixture, 1 μl of the mixed primer 1, 1 μl of the primer C1 (a primer attached to LA PCR in vitro cloning kit (Takara Shuzo)), 0.5 μl of TaKaRa LA Taq and sterile water to 50 μl were added thereto. After the solution was overlaid with 50 μl of mineral oil, the tube was subjected to a reaction using an automated gene amplification instrument Thermal Cycler (Takara Shuzo). After denaturing at 94° C. for 2 minutes, a PCR of 30 cycles was performed. Each cycle consisted of denaturation at 94° C. for 1 minute, annealing of primers at 50° C. for 2 minutes and synthesis reaction at 72° C. for 2 minutes.

Next, a secondary PCR was carried out using the reaction mixture as a template. A PCR was carried out under the same conditions as those for the primary PCR except that 1 μl of the reaction mixture obtained by the primary PCR as a template, as well as a combination of the mixed primer 2 and the primer C2 (a primer attached to LA PCR in vitro cloning kit (Takara Shuzo)) were used. After the PCR, the mineral oil upper layer was removed and 5 μl of the reaction mixture was subjected to electrophoresis on a 1.0% agarose gel followed by staining of the DNA with ethidium bromide to confirm the amplification product. As a result, a DNA fragment of about 0.8 kb was observed. The DNA fragment was designated as βN.

The amplified fragment βN excised from the agarose gel was ligated to a vector pT7Blue and used to transform *Escherichia coli* JM109. Nucleotide sequences of the terminal regions of the amplified fragment βN were determined using a transformant according to the dideoxy chain terminator method. Primers 3 and 4 (SEQ ID NOS:10 and 11) were designed based on the sequence of the N-terminal region. Primers 5 and 6 (SEQ ID NOS:12 and 13) were designed based on the sequence of the terminal region other than the N-terminal region. They were synthesized using a DNA synthesizer and then purified. DNA fragments upstream and downstream of βN were cloned in a similar manner utilizing these primers and LA PCR in vitro cloning kit (Takara Shuzo). In this case, primers were annealed at 55° C. for 1 minute.

For the upstream region, the primers 3 and 4 were utilized to obtain a DNA fragment of about 0.6 kb, which was designated as βUN. For the region downstream of βN, the primers 5 and 6 were utilized to obtain a DNA fragment of about 1.3 kb, which was designated as βC. Both βUN and βC were ligated to the vector pT7Blue (Novagen). The nucleotide sequences were determined according to the dideoxy chain terminator method. The nucleotide sequences of the DNA fragments βN, βUN and βC were analyzed and aligned. As a result, an ORF that encodes a protein consisting of 438 amino acids was found.

The nucleotide sequence of the ORF and the amino acid sequence encoded by the nucleotide sequence of the ORF are shown in SEQ ID NOS:20 and 22, respectively. It was found that, in βUN, there exist a nucleotide sequence for the amino acid sequence P1, a nucleotide sequence that encodes 20 amino acids upstream from the amino acid sequence P1, and an SD-like sequence in a further upstream region.

The N-terminal amino acid sequence P1 determined in Example 3 corresponds to the sequence of the 21st to 33rd amino acids in SEQ ID NO:22. The partial amino acid sequences PI3 (SEQ ID NO:3) and PI4 (SEQ ID NO:4) determined in Example 3 match to the sequences of the 265th to 272nd amino acids and the 367th to 376th amino acids in SEQ ID NO:22, respectively.

Example 9

Cloning of Agarase II Gene

Mixed primers 7 and 8 (SEQ ID NOS:14 and 15) were designed on the basis of the N-terminal amino acid sequence of Agarase II, P2 (SEQ ID NO:2) and PII6 (SEQ ID NO:6), which were determined as described in Example 3. They hybridize to strands different from each other. The mixed primers were synthesized using a DNA synthesizer and then purified.

Specifically, the mixed primer 7 represented by SEQ ID NO:14 corresponds to amino acid numbers 1-8 in the amino acid sequence P2, and the mixed primer 8 represented by SEQ ID NO:15 corresponds to a complementary strand of a DNA encoding amino acid numbers 2-10 in the amino acid sequence PII6.

Cloning of the Agarase II gene was carried out using these primers and LA PCR in vitro cloning kit (Takara Shuzo).

A primary PCR was carried out as follows. 10 ng of the NAB2-1-1 chromosomal DNA prepared in Example 7 was placed in a 0.5-ml tube for PCR. 5 μl of 10×LA PCR buffer, 8 μl of a dNTP mixture, 40 μmol each of the mixed primers 7 and 8, 0.5 μl of TaKaRa LA Taq and sterile water to 50 μl were added thereto. After the solution was overlaid with 50 μl of mineral oil, the tube was subjected to a reaction using an automated gene amplification instrument Thermal Cycler (Takara Shuzo). After denaturing at 94° C. for 2 minutes, a PCR of 30 cycles was performed. Each cycle consisted of denaturation at 94° C. for 1 minute, annealing of primers at 50° C. for 2 minutes and synthesis reaction at 72° C. for 2 minutes. The mineral oil upper layer was removed and 5 μl of the reaction mixture was subjected to electrophoresis on a 1.0% agarose gel followed by staining of the DNA with ethidium bromide to confirm the amplification product. As a result, a DNA fragment of about 600 bp was observed. The DNA fragment was designated as αN.

The amplified fragment αN excised from the agarose gel was ligated to the vector pT7Blue and used to transform *Escherichia coli* JM109. The nucleotide sequences of the terminal regions of the amplified fragment aN were determined using a transformant according to the dideoxy chain terminator method. Primers 9 and 10 (SEQ ID NOS:16 and 17) were designed based on the sequence of the N-terminal region. Primers 11 and 12 (SEQ ID NOS:18 and 19) were designed based on the sequence of the terminal region other than the N-terminal region. They were synthesized using a DNA synthesizer and then purified. DNA fragments upstream and downstream of αN were cloned in a similar manner utilizing these primers and LA PCR in vitro cloning kit (Takara Shuzo).

In this case, a PCR was carried out as follows. The NAB2-1-1 chromosomal DNA prepared in Example 7 was completely digested with a restriction enzyme BamHI. A BamHI adaptor was ligated to the termini of the digested DNA using DNA Ligation Kit (Takara Shuzo). A portion thereof was placed in a 0.5-ml tube for PCR. 5 µl of 10×LA PCR buffer, 8 µl of a dNTP mixture, 1 µl of the primer 9, 1 µl of the primer C1, 0.5 µl of TaKaRa LA Taq and sterile water to 50 µl were added thereto. After the solution was overlaid with 50 µl of mineral oil, the tube was subjected to a reaction using an automated gene amplification instrument Thermal Cycler (Takara Shuzo). After denaturing at 94° C. for 2 minutes, a PCR of 30 cycles was performed. Each cycle consisted of denaturation at 94° C. for 1 minute, annealing of primers at 50° C. for 2 minutes and synthesis reaction at 72° C. for 3 minutes.

Next, a secondary PCR was carried out using the reaction mixture as a template. A PCR was carried out under the same conditions as those for the primary PCR except that 1 µl of the reaction mixture obtained by the primary PCR as a template, as well as a combination of the primer 10 and the primer C2 were used. The mineral oil upper layer was removed and 5 µl of the reaction mixture was subjected to electrophoresis on a 1.0% agarose gel followed by staining of the DNA with ethidium bromide to confirm the amplification product. As a result, a DNA fragment of about 500 bp was observed. The DNA fragment was designated as αUN.

Similarly, the primers 11 and 12 were used to obtain an about 2-kb DNA fragment downstream of αN, which was designated as αC. Both αUN and αC were ligated to the vector pT7Blue (Novagen). The nucleotide sequences were determined according to the dideoxy chain terminator method. The nucleotide sequences of the DNA fragments αN, αUN and αC were analyzed and aligned. As a result, an ORF that encodes a protein consisting of 1089 amino acids was found.

The nucleotide sequence of the ORF and the amino acid sequence encoded by the nucleotide sequence of the ORF are shown in SEQ ID NOS:21 and 23, respectively. It was found that, in αUN, there exist a nucleotide sequence for the amino acid sequence P2, a nucleotide sequence that encodes 26 amino acids having a signal peptide-like sequence upstream from the amino acid sequence P2, and an SD-like sequence in a further upstream region.

The amino acid sequence P2 corresponds to the sequence of the 27th to 36th amino acids in SEQ ID NO:23. The partial amino acid sequences PII5 (SEQ ID NO:5), PII6 (SEQ ID NO:6) and PII7 (SEQ ID NO:7) determined in Example 3 match to the sequences of the 129th to 138th amino acids, the 640th to 649th amino acids and the 738th to 747th amino acids in SEQ ID NO:23, respectively.

Furthermore, three putative Ca-binding regions (171-184, 271-283 and 987-999 in SEQ ID NO:23) were found.

Example 10

Construction of Plasmid for Expressing Agarase I

A primer 13 (SEQ ID NO:24) is a synthetic DNA that has a recognition sequence for a restriction enzyme EcoRI at nucleotide numbers 12 to 17 and a nucleotide sequence corresponding to amino acid numbers 21 to 27 in the amino acid sequence of SEQ ID NO:22 at nucleotide numbers 19 to 38. A PCR was carried out as follows using the primer 13 and a primer 14 (SEQ ID NO:25) which has a recognition sequence for a restriction enzyme PstI at nucleotide numbers 11 to 16 and hybridizes to a strand complementary to a portion about 300 bp downstream from the reading frame for Agarase I on the chromosome. 10 pmol each of the primers 13 and 14, 10 ng of the chromosomal DNA from NAB2-1-1 as a template, 5 µl of 10× ExTaq buffer, 8 µl of a dNTP mixture, 0.5 µl of TaKaRa ExTaq and sterile water to 50 µl were added to a 0.5-ml tube for PCR. The tube was placed in an automated gene amplification instrument Thermal Cycler (Takara Shuzo). After denaturing at 94° C. for 2 minutes, a PCR of 25 cycles was performed. Each cycle consisted of 94° C. for 1 minute, 55° C. for 2 minutes and 72° C. for 2 minutes. The PCR product was concentrated and desalted by ethanol precipitation, doubly digested with restriction enzymes EcoRI (Takara Shuzo) and PstI (Takara Shuzo), and then subjected to electrophoresis on a 1.0% agarose gel. The EcoRI-PstI digest was extracted and purified. The purified product was mixed with pUC18 (Takara Shuzo) which had been digested with the same enzymes and ligation was carried out using DNA Ligation Kit (Takara Shuzo). 10 µl of the ligation mixture was used to transform *Escherichia coli* JM109. Transformants were grown on LB medium containing agar at a concentration of 1.5% (w/v) and ampicillin at a concentration of 50 µg/ml. Plasmids were prepared from white colonies, and DNA sequencing was carried out. A plasmid into which the PCR product was properly inserted was selected and designated as pNB101. pNB101 is a plasmid that encodes an amino acid sequence of amino acid numbers 21 to 437 in the amino acid sequence of Agarase I (SEQ ID NO:22). *Escherichia coli* transformed with the plasmid pNB101 was designated as *Escherichia coli* JM109/pNB101 and deposited on Jan. 10, 2001 (the date of the original deposit) at International Patent Organism Depositary, National Institute of Advanced Industrial Science and Technology, AIST Tsukuba Central 6, 1-1, Higashi 1-chome, Tsukuba-shi, Ibaraki 305-8566, Japan under accession number FERM BP-7854.

The transformant having pNB101 being introduced was inoculated into 2.5 ml of LB broth containing 50 µg/ml of ampicillin and cultured at 37° C. overnight. A portion of the culture was inoculated into 2.5 ml of the same fresh medium and cultured at 37° C. until it reached exponential growth phase. At that time, IPTG was added thereto at a final concentration of 1.0 mM. The cultivation was continued at a temperature of 20° C. for additional two hours to induce the expression of the protein of interest. The cells were then collected by centrifugation and resuspended in 150 µl of a cell destruction solution (20 mM Tris-HCl buffer (pH 7.2) containing 10 mM sodium chloride). The cells were destroyed by sonication. An extract as a supernatant and a precipitate were separated from each other by centrifugation and used as samples for the measurements of β-agarase activities using agarose as a substrate. Then, an activity was observed for the extract as a supernatant. The activity contained in 100 ml of the culture was about 25-fold higher than that of the wild type strain NAB2-1-1.

Example 11

Expression System for Agarase I Using pET16b

A PCR was carried out using a primer 15 (SEQ ID NO:26) and a primer 16 (SEQ ID NO:27) as well as the NAB2-1-1 chromosomal DNA as a template under conditions as described in Example 10. The primer 15 is a primer that has a nucleotide sequence corresponding to amino acid numbers 21 to 27 in the amino acid sequence of Agarase I (SEQ ID NO:22) at nucleotide numbers 20 to 39 and a recognition sequence for a restriction enzyme NdeI at nucleotide numbers 14 to 19. The primer 16 is a primer that has a recognition sequence for a restriction enzyme XhoI at nucleotide numbers 12 to 17 and hybridizes to a strand complementary to a portion about 300 bp downstream from the reading frame for Agarase I on the chromosome. The amplified fragment was concentrated by ethanol precipitation, digested with NdeI (Takara Shuzo) and XhoI (Takara Shuzo), extracted and purified. The product was ligated to pET16b (Takara Shuzo) which had been digested with the same enzymes. The resulting plasmid was designated as pNB201. pNB201 is a plasmid that encodes an amino acid sequence of amino acid numbers 21 to 437 in the amino acid sequence of Agarase I (SEQ ID NO:22).

pNB201 was used to transform *Escherichia coli* BL21 (DE3) pLysS and the resulting transformant was used for determination of a β-agarase activity as described above in Example 10. Then, an activity was observed for the extract. The activity contained in 100 ml of the culture was about 50-fold higher than that of NAB2-1-1.

Example 12

Construction of Plasmid for Expressing Agarase II

A primer 17 (SEQ ID NO:28) is a synthetic DNA that has a recognition sequence for a restriction enzyme EcoRI at nucleotide numbers 10 to 15 and a nucleotide sequence corresponding to amino acid numbers 27 to 33 in the amino acid sequence of Agarase II (SEQ ID NO:23) at nucleotide numbers 17 to 37. A PCR was carried out using the primer 17 and a primer 18 (SEQ ID NO:29) which has a recognition sequence for a restriction enzyme BamHI at nucleotide numbers 11 to 16 and hybridizes to a portion about 250 bp downstream from the reading frame for Agarase II on the chromosome. 10 pmol each of the primers 17 and 18 as well as 10 ng of the chromosomal DNA from a wild type strain NAB2-1-1 as a template were used for the PCR in a reaction system using ExTaq (Takara Shuzo). After denaturing at 94° C. for 2 minutes, a PCR of 30 cycles was performed. Each cycle consisted of 94° C. for 1 minute, 50° C. for 2 minutes and 72° C. for 3 minutes. The PCR product was concentrated by ethanol precipitation, doubly digested with restriction enzymes EcoRI (Takara Shuzo) and BamHI (Takara Shuzo), and then subjected to electrophoresis on a 1.0% agarose gel. The EcoRI-BamHI digest was extracted and purified. A hybrid plasmid with pUC18 was constructed as described in Example 10, and used to transform *Escherichia coli* JM109. The hybrid plasmid was designated as pNA101. pNA101 is a plasmid that encodes an amino acid sequence of amino acid numbers 27 to 1089 in the amino acid sequence of Agarase II (SEQ ID NO:23).

*Escherichia coli* transformed with the plasmid pNA101 was designated as *Escherichia coli* JM109/pNA101 and deposited on Jan. 10, 2001 (the date of the original deposit) at International Patent Organism Depositary, National Institute of Advanced Industrial Science and Technology, AIST Tsukuba Central 6, 1-1, Higashi 1-chome, Tsukuba-shi, Ibaraki 305-8566, Japan under accession number FERM BP-7853.

The transformant having pNA101 being introduced was subjected to measurements of α-agarase activities as described in Example 10 except that 10 mM calcium chloride was included in the cell destruction product. An activity was observed for the extract. The activity contained in 100 ml of the culture was about 15-fold higher than that of the wild type strain NAB2-1-1.

Example 13

Activity of Agarase II Protein with Deletion

A modified protein was prepared by means of genetic engineering as described below. The α-agarase activity of the modified protein was determined.

A primer 19 (SEQ ID NO:30) is a primer that has a nucleotide sequence corresponding to amino acid numbers 181 to 188 in the amino acid sequence of Agarase II (SEQ ID NO:23) at nucleotide numbers 19 to 40 and a recognition sequence for a restriction enzyme EcoRI at nucleotide numbers 12 to 17.

A PCR was carried out using the primer 19 and the primer 18 (SEQ ID NO:29) as well as the NAB2-1-1 chromosomal DNA as a template. The product was ligated to pUC18, and transformation of *Escherichia coli* JM109 was carried out as described in Example 12. A hybrid plasmid obtained by confirming the DNA sequence at the connection site was designated as pNA201d. A protein expressed from pNA201d is one in which a portion up to amino acid number 180 in the amino acid sequence of Agarase II (SEQ ID NO:23) is deleted. In other words, pNA201d is a plasmid that encodes an amino acid sequence of amino acid numbers 181 to 1089 in the amino acid sequence of Agarase II (SEQ ID NO:23). After induction of expression using IPTG, measurements of activities were carried out as described in Example 10 except that 10 mM calcium chloride was included in the cell destruction product. An α-agarase activity was observed for the extract. The activity contained in 100 ml of the culture was about 2-fold higher than that of NAB2-1-1.

A primer 20 (SEQ ID NO:31) has a nucleotide sequence corresponding to amino acid numbers 318 to 325 in the amino acid sequence of Agarase II (SEQ ID NO:23) at nucleotide numbers 19 to 40 and a recognition sequence for a restriction enzyme EcoRI at nucleotide numbers 12 to 17. A PCR was carried out using the primer 20 and the primer 18 (SEQ ID NO:29) as well as the NAB2-1-1 chromosomal DNA as a template to construct a hybrid plasmid with pUC18, pNA301d. A protein in which a peptide up to amino acid number 317 in the amino acid sequence of Agarase II (SEQ ID NO:23) is deleted is expressed from *Escherichia coli* JM109 having pNA301d being introduced. In other words, pNA301d is a plasmid that encodes an amino acid sequence of amino acid numbers 318 to 1089 in the amino acid sequence of Agarase II (SEQ ID NO:23). Measurements of activities were carried out as described in Example 10 except that 10 mM calcium chloride was included in the cell destruction product. An α-agarase activity was observed for the extract. The activity contained in 100 ml of the culture was about 15-fold higher than that of NAB2-1-1. Furthermore, an extract derived from a transformant having pNA301d being introduced was dialyzed against a calcium-free buffer (20 mM Tris-HCl buffer (pH 7.2) containing 10 mM sodium chloride and 1 mM EDTA (pH 7.2)) and then reacted with a solution containing agarose at a concentration of 0.2% in 20 mM Tris-HCl buffer (pH 7.2) containing 10 mM sodium chloride and 1 mM EDTA (pH 7.2). As a result, a digestion activity similar to that observed using a buffer containing calcium was observed.

Example 14

Comparison with AgarACE Enzyme (Promega)

[Optimal Temperature]

The enzymological properties of Agarase I of the present invention were compared with those of the AgarACE enzyme, a β-agarase derived from marine *Flavobacterium* which is sold by Promega.

10 μl of Agarase I or the AgarACE enzyme (Promega; corresponding to 0.29 units according to the attached data sheet) was added to 40 μl of 1.0% (w/v) NuSieve GTG Agarose dissolved by heating in 20 mM Tris-HCl buffer (pH 7.3) (FMC). The mixture was reacted at 45° C., 50° C., 55° C., 60° C. or 65° C. for 10 minutes. The activities of both enzymes had been measured beforehand according to the method as described in Example 1. Then, the enzymes were added such that same enzymatic activities were included in the respective reactions. After reaction, the enzymatic activities were calculated as described in Example 1. Defining the maximal enzymatic activity as 100%, results expressed as relative values are shown in Table 3. As seen from the results, the optimal temperature of Agarase I was 50° C. to 65° C. and the optimal temperature of the AgarACE enzyme was 45° C. to 50° C.

TABLE 3

| | Relative activity (%) | | | | | |
|---|---|---|---|---|---|---|
| | 45° C. | 50° C. | 55° C. | 60° C. | 65° C. | 70° C. |
| Agarase I | 89 | 97 | 100 | 100 | 100 | 95 |
| AgarACE | 100 | 98 | 84 | 25 | 11 | 0 |

[Thermostability]

10 μl of Agarase I or the AgarACE enzyme (corresponding to 0.29 units according to the attached data sheet) was incubated at 60° C. or 65° C. for a given period, and then added to 40 μl of 1.0% (w/v) NuSieve GTG Agarose dissolved by heating in 20 mM Tris-HCl buffer (pH 7.3) (FMC). The enzymes were added such that same enzymatic activities were included in the respective reactions as described above. The mixture was reacted at 55° C. for 10 minutes (in case of Agarase I) or 45° C. for 10 minutes (in case of the AgarACE enzyme). The enzymatic activities were calculated as described in Example 1. Defining the activity observed without heating as 100%, results expressed as relative values are shown in Table 4. As seen from the results, almost 100% of the activity of Agarase I was retained after incubation at 65° C. for 10 minutes, while the AgarACE enzyme was completely inactivated after incubation at 65° C. for 10 minutes.

TABLE 4

| | Remaining activity (%) | | | |
|---|---|---|---|---|
| Incubation time (min) | 0 | 10 | 20 | 30 |
| Agarase I | | | | |
| (60° C.) | 100 | 100 | 100 | 98 |
| (65° C.) | 100 | 100 | 95 | 90 |
| AgarACE | | | | |
| (60° C.) | 100 | 81 | 48 | 21 |
| (65° C.) | 100 | 3 | 0 | 0 |

Example 15

Change in Thermostability of Enzyme Due to Calcium

*Escherichia coli* JM109 transformed with pNA101 (Example 11) or pNA301d (Example 13) was inoculated into 2.5 ml of LB broth containing 50 μg/ml of ampicillin and cultured at 37° C. overnight. A portion of the culture was inoculated into 100 ml of the same medium and cultured at 37° C. until it reached exponential growth phase. At that time, IPTG was added thereto at a final concentration of 1.0 mM. The cultivation was continued at a temperature of 20° C. for additional two hours to induce the expression of the protein of interest. The cells were then collected by centrifugation and suspended in 5 ml of a cell destruction solution (20 mM Tris-HCl buffer (pH 7.2) containing 10 mM sodium chloride and 1 mM calcium chloride). The cells were destroyed by sonication. A supernatant was collected by centrifugation. The α-agarase activity in the supernatant was measured. The supernatant was diluted with the cell destruction solution such that the same enzymatic activity was contained in a unit volume for each sample. The thus obtained extract for each enzyme was dialyzed overnight against Buffer A (20 mM Tris-HCl buffer (pH 7.2) containing 10 mM sodium chloride and 10 mM calcium chloride) which contained calcium, or Buffer B (20 mM Tris-HCl (pH 7.2) containing 10 mM sodium chloride and 1 mM EDTA (pH 7.2)) which did not contain calcium. 20 μl of the enzyme solution was incubated at 55° C. or 50° C. for 10 minutes and then reacted with 180 μl of a solution containing agarose at a concentration of 0.2% in 20 mM Tris-HCl buffer (pH 7.2) containing 10 mM sodium chloride. The remaining α-agarase activity was measured according to the method as described in Example 1. The results are shown in Table 5.

Native Agarase II obtained from NAB2-1-1 was used as a control.

TABLE 5

| | Remaining activity (%)* | | | |
|---|---|---|---|---|
| Treatment temperature | 50° C. | | 55° C. | |
| Buffer | A | B | A | B |
| Native Agarase II | 100 | 56 | 42 | 10 |
| pNA101 | 100 | 60 | 45 | 15 |
| pNA301d | 100 | 58 | 70 | 12 |

*The remaining activity after treatment at 50° C. in Buffer A for each enzyme was defined as 100.

Example 15

Activity of Agarase II Protein with Deletion

A modified protein was prepared by means of genetic engineering as described below. The α-agarase activity of the modified protein was determined.

A primer 21 (SEQ ID NO:34) has a nucleotide sequence corresponding to amino acid numbers 290 to 297 in the amino acid sequence of Agarase II (SEQ ID NO:23) at nucleotide numbers 19 to 40 and a recognition sequence for a restriction enzyme EcoRI at nucleotide numbers 12 to 17.

A PCR was carried out using the primer 21 and the primer 18 (SEQ ID NO:29) as well as the NAB2-1-1 chromosomal DNA as a template. The product was ligated to pUC18, and transformation of Escherichia coli JM109 was carried out as described in Example 12. A hybrid plasmid obtained by confirming the DNA sequence at the connection site was designated as pNA401d. A protein expressed from pNA401d is one in which a portion up to amino acid number 289 in the amino acid sequence of Agarase II (SEQ ID NO:23) is deleted. In other words, pNA401d is a plasmid that encodes an amino acid sequence of amino acid numbers 290 to 1089 in the amino acid sequence of Agarase II (SEQ ID NO:23). Escherichia coli JM109 transformed with pNA301d obtained in Example 13 or pNA401d obtained as described above was inoculated into 2.5 ml of LB broth containing 50 μg/ml of ampicillin and cultured at 37° C. overnight. A portion of the culture was inoculated into 100 ml of the same medium and cultured at 37° C. until it reached exponential growth phase. At that time, IPTG was added thereto at a final concentration of 1.0 mM. The cultivation was continued at a temperature of 20° C. for additional two hours to induce the expression of the protein of interest. The cells were then collected by centrifugation and suspended in 5 ml of a cell destruction solution (20 mM Tris-HCl buffer (pH 7.2) containing 10 mM sodium chloride and 10 mM calcium chloride). The cells were destroyed by sonication. A supernatant was collected by centrifugation. The α-agarase activity in the supernatant was measured. The supernatant was diluted with the cell destruction solution such that the same enzymatic activity was contained in a unit volume for each sample. 20 μl of the enzyme solution was incubated at 55° C. or 60° C. for 10 minutes and then reacted with 180 μl of a solution containing agarose at a concentration of 0.2% in 20 mM Tris-HCl buffer (pH 7.2) containing 10 mM sodium chloride. The remaining α-agarase activity was measured according to the method as described in Example 1. The results are shown in Table 6. These results show that the thermostability of the product of pNA401d is equal to or higher than that of pNA301d.

Native Agarase II obtained from NAB2-1-1 was used as a control.

TABLE 6

|  | Remaining activity (%)* | |
|---|---|---|
| Treatment temperature | 55° C. | 60° C. |
| Native Agarase II | 42 | 0 |
| pNA301d | 70 | 31 |
| pNA401d | 79 | 39 |

*The remaining activity after treatment at 50° C. for each enzyme was defined as 100.

Furthermore, a supernatant was collected by centrifugation after induction with IPTG at 37° C. overnight followed by destruction of cells by sonication as described above. The protein content of the supernatant was quantified. The supernatant was subjected to SDS-PAGE such that the same amount of protein was loaded. In addition, the precipitate obtained upon collection of the supernatant was suspended in the cell destruction solution and subjected to SDS-PAGE in a similar manner. As a result, it was found that the amount of the protein of interest in the supernatant obtained using pNA401d with induction was greater than the amount of the protein of interest in the supernatant obtained using the native type or pNA301d. Thus, it was shown that the mutant α-agarase expressed by induction from Escherichia coli JM109 transformed with pNA401d was readily solubilized.

INDUSTRIAL APPLICABILITY

The present invention provides a novel agarase. The optimal temperature of the agarase of the present invention is higher than that of a conventional agarase and the agarase is excellently thermostable. Therefore, it can be used for a reaction at a high temperature. Accordingly, the agarase of the present invention is excellently effective in that it enables a reaction in the presence of agarose at a high concentration without solidification.

It is possible to efficiently produce agarooligosaccharides with low degrees of polymerization having 3,6-anhydro-L-galactose at their reducing ends (e.g., agarobiose and agarotetraose) or neoagarooligosaccharides having 3,6-anhydro-L-galactose at their nonreducing ends (e.g., neoagarobiose and neoagarotetraose) directly from agarose by using the agarase of the present invention.

A nucleic acid or the like can be efficiently extracted from an agarose gel by using the agarase of the present invention.

The agarooligosaccharides produced using the agarase of the present invention have physiological activities such as an apoptosis-inducing activity, a carcinostatic activity, various antioxidant activities, an immunoregulatory activity and an antiallergic activity. Thus, they are useful in the fields of pharmaceutical compositions, foods and drinks.

The present invention discloses the amino acid sequence and the nucleotide sequence for the agarase for the first time. Thus, it is possible to provide a gene encoding a polypeptide having an agarase activity. The present invention also provides an industrially advantageous method for producing a polypeptide having an agarase activity by genetic engineering using said gene.

Furthermore, addition of agarose to a medium for inducing the production of the agarase is not required in the production method by genetic engineering using said gene. Thus, it is considered that labor can be saved upon cultivation and the enzyme is readily purified.

In addition, based on the fact that the present invention provides the agarase gene for the first time, the present invention provides, based on the information on said gene, a recombinant polypeptide encoded by the gene, an antibody that specifically binds to the polypeptide or a fragment thereof, as well as a probe or a primer that specifically hybridize to the agarase.

Sequence Listing Free Text

SEQ ID No:1: N-terminal amino acid sequence of agarase I

SEQ ID No:2: N-terminal amino acid sequence of agarase II

SEQ ID No:3: Partial amino acid sequence of agarase I
SEQ ID No:4: Partial amino acid sequence of agarase I
SEQ ID No:5: Partial amino acid sequence of agarase II
SEQ ID No:6: Partial amino acid sequence of agarase II SEQ ID No:7: Partial amino acid sequence of agarase II
SEQ ID No:8: PCR primer 1
SEQ ID No:9: PCR primer 2
SEQ ID No:10: PCR primer 3
SEQ ID No:11: PCR primer 4
SEQ ID No:12: PCR primer 5
SEQ ID No:13: PCR primer 6
SEQ ID No:14: PCR primer 7
SEQ ID No:15: PCR primer 8
SEQ ID No:16: PCR primer 9
SEQ ID No:17: PCR primer 10
SEQ ID No:18: PCR primer 11
SEQ ID No:19: PCR primer 12
SEQ ID No:20: Nucleotide sequence of ORF in agarase I
SEQ ID No:21: Nucleotide sequence of ORF in agarase II
SEQ ID No:22: Amino acid sequence of agarase I
SEQ ID No:23: Amino acid sequence of agarase II
SEQ ID No:24: PCR primer 13
SEQ ID No:25: PCR primer 14
SEQ ID No:26: PCR primer 15
SEQ ID No:27: PCR primer 16
SEQ ID No:28: PCR primer 17
SEQ ID No:29: PCR primer 18
SEQ ID No:30: PCR primer 19
SEQ ID No:31: PCR primer 20
SEQ ID No:32: Designed oligonucleotide primer for amplifying DNA fragment from 16S ribosomal
SEQ ID No:33: Designed oligonucleotide primer for amplifying DNA fragment from 16S ribosomal
SEQ ID No. 34: PCR primer 21

The invention claimed is:

1. An isolated agarase which comprises the amino acid sequence of 417 residues from residue 21 to residue 437 in the amino acid sequence of SEQ ID NO:22, or an amino acid sequence that is encoded by a DNA which hybridizes to the nucleotide sequence of 1251 nucleotides from nucleotide 61 to nucleotide 1311 in the nucleotide sequence of SEQ ID NO:20 in a solution containing 6×SSC (1×SSC: 0.15 M NaCl, 0.015 M sodium citrate, pH 7.0), 0.5% SDS, 5×Denhardt's and 100 mg/ml herring sperm DNA at 65° C. and has an activity of hydrolyzing a β-1,4 bond between D-galactose and 3,6-anhydro-L-galactose in agarose.

2. The agarase according to claim 1, which is obtainable from a microorganism NAB2-1-1 (FERM BP-7855).

3. An isolated gene encoding the agarase defined by claim 1.

4. The gene according to claim 3, which is obtainable from a microorganism NAB2-1-1 (FERM BP-7855).

5. The gene according to claim 3, which comprises the nucleotide sequence of 1251 nucleotides from nucleotide number 61 to nucleotide number 1311 in the nucleotide sequence of SEQ ID NO:20.

6. An isolated gene which hybridizes to a gene encoding the agarase which comprises the amino acid sequence of 417 residues from residue 21 to residue 437 in the amino acid sequence of SEQ ID NO:22 in a solution containing 6×SSC (1×SSC: 0.15M NaCl, 0.015M sodium citrate, pH 7.0), 0.5% SDS, 5×Denhardt's and 100 mg/ml herring sperm DNA at 65° C. and which encodes an agarase having an activity of hydrolyzing a β-1,4 bond between D-galactose and 3,6-anhydro-L-galactose in agarose.

7. A recombinant DNA molecule which comprises a gene selected from the group consisting of:

(a) a gene encoding an agarase which comprises the amino acid sequence of 417 residues from residue 21 to residue 437 in the amino acid sequence of SEQ ID NO:22, and has an activity of hydrolyzing a β-1,4 bond between D-galactose and 3,6-anhydro-L-galactose in agarose; and (b) a gene which hybridizes to the gene of (a) in a solution containing 6×SSC (1×SSC: 0.15 M NaCl, 0.015 M sodium citrate, pH 7.0), 0.5% SDS, 5×Denhardt's and 100 mg/ml herring sperm DNA at 65° C. and encodes an agarase having an activity of hydrolyzing a β-1,4 bond between D-galactose and 3,6-anhydro-L-galactose in agarose.

8. An isolated host cell transformed with the recombinant DNA molecule defined by claim 7.

9. A method for producing the agarase defined by claim 1, the method comprising culturing a microorganism NAB2-1-1 (FERM BP-7855); and collecting the agarase from the culture.

10. A method for producing an agarase, the method comprising culturing the host cell defined by claim 8; and collecting an agarase from the culture.

11. A method for producing an agarooligosaccharide, the method comprising digesting agarose with the agarase defined by claim 1; and collecting an agarooligosaccharide from the digest.

12. A kit used for the method for extracting a material from an agarose gel which comprises digesting the agarose gel with an agarase, comprising the agarase defined by claim 1.

13. The agarase of claim 1, which comprises the amino acid sequence of 417 residues from residue 21 to residue 437 in the amino acid sequence of SEQ ID NO:22.

14. An isolated gene encoding the agarase defined by claim 13.

15. The recombinant DNA molecule of claim 7, which comprises a gene encoding an agarase which comprises the amino acid sequence of 417 residues from residue 21 to residue 437 in the amino acid sequence of SEQ ID NO:22 and has an activity of hydrolyzing a β-1,4 bond between D-galactose and 3,6-anhydro-L-galactose in agarose.

16. An isolated host cell transformed with the recombinant DNA molecule defined by claim 15.

17. A method for producing agarase, the method comprising culturing the host cell defined by claim 16; and collecting the agarase from the culture.

* * * * *